(12) United States Patent
Daniell

(10) Patent No.: US 10,752,909 B2
(45) Date of Patent: Aug. 25, 2020

(54) CHLOROPLASTS ENGINEERED TO EXPRESS PHARMACEUTICAL PROTEINS IN EDIBLE PLANTS

(75) Inventor: Henry Daniell, Winter Park, FL (US)

(73) Assignee: The Trustees of the University of Pennsylvania, Philadelphia, PA (US)

(*) Notice: Subject to any disclaimer, the term of this patent is extended or adjusted under 35 U.S.C. 154(b) by 0 days.

(21) Appl. No.: 12/059,376

(22) Filed: Mar. 31, 2008

(65) Prior Publication Data

US 2009/0022705 A1 Jan. 22, 2009

Related U.S. Application Data

(60) Provisional application No. 60/909,158, filed on Mar. 30, 2007.

(51) Int. Cl.
*C12N 15/82* (2006.01)

(52) U.S. Cl.
CPC ..... *C12N 15/8214* (2013.01); *C12N 15/8258* (2013.01)

(58) Field of Classification Search
None
See application file for complete search history.

(56) References Cited

U.S. PATENT DOCUMENTS

| 4,235,871 | A | * | 11/1980 | Papahadjopoulos et al. ............ 424/450 |
| 5,693,507 | A | | 12/1997 | Daniell |
| 5,877,402 | A | * | 3/1999 | Maliga et al. ................ 800/298 |
| 5,914,123 | A | | 6/1999 | Arntzen et al. |
| 5,932,479 | A | | 8/1999 | Daniell |
| 6,642,053 | B1 | | 11/2003 | Daniell |
| 6,680,426 | B2 | | 1/2004 | Daniell |
| 7,129,391 | B1 | | 10/2006 | Daniell |
| 7,135,620 | B2 | | 11/2006 | Daniell |
| 7,294,506 | B2 | * | 11/2007 | Daniell et al. ............. 435/320.1 |
| 7,354,760 | B2 | * | 4/2008 | Daniell ...................... 435/320.1 |
| 2002/0137214 | A1 | * | 9/2002 | Daniell ........................ 435/468 |
| 2002/0162135 | A1 | | 10/2002 | Daniell |
| 2003/0204864 | A1 | | 10/2003 | Daniell |
| 2004/0177402 | A1 | | 9/2004 | Daniell |
| 2004/0199939 | A1 | | 10/2004 | Chan et al. |
| 2005/0044588 | A1 | | 2/2005 | Langridge et al. |
| 2005/0108792 | A1 | | 5/2005 | Daniell |
| 2006/0117412 | A1 | | 6/2006 | Daniell |
| 2006/0130178 | A1 | | 6/2006 | Keetman et al. |
| 2006/0185034 | A1 | | 8/2006 | Todd et al. |
| 2006/0253935 | A1 | | 11/2006 | Daniell |
| 2007/0067862 | A1 | | 3/2007 | Daniell |
| 2007/0124830 | A1 | | 5/2007 | Daniell |
| 2007/0124838 | A1 | | 5/2007 | Daniell |
| 2008/0241916 | A1 | | 2/2008 | Daniell |

FOREIGN PATENT DOCUMENTS

| CN | 1429906 | * | 7/2003 |
| WO | 1999010513 | | 4/1999 |
| WO | 2001072959 | | 4/2001 |
| WO | 2001064023 | | 7/2001 |
| WO | 2001064850 | | 9/2001 |
| WO | 2001064927 | | 9/2001 |
| WO | 2001064929 | | 9/2001 |
| WO | 2003057834 | | 7/2003 |
| WO | 2004005467 | | 1/2004 |
| WO | 2004005480 | | 1/2004 |
| WO | 2004005521 | | 1/2004 |
| WO | 2006027865 | | 3/2006 |
| WO | WO 2006/027865 | * | 3/2006 |
| WO | WO2007053182 | | 5/2007 |
| WO | WO2007053183 | | 5/2007 |
| WO | 2007053183 | | 10/2007 |

OTHER PUBLICATIONS

Lelivelt et al (2005, Plant Mol. Biol. 58:763-774).*
Molina et al (2004, Plant Biotechnol. J. 2:141-153).*
Kumar et al (2004, Methods Mol. Biol. 267:365-383).*
Daniell et al (2005, Vaccine 23:1779-1783).*
English translation of Zhou et al (2003, CN 1429906).*
Arakawa et al (1998, Nature Biotechnol. 16:934-938).*
Kanamoto et al (2006, Transgenic Res. 15:206-217).*
Tian et al, 2011, Int. J. Mol. Sci. 12:1060-1065.*
Zou et al (2003, Mol. Gen. Genomics. 269:340-349).*
Shi et al (2001, http://www.ebi.ac.uk/ena/data/view/ AF426317 &display=text).*
Daniell, H. "Production of Biopharmaceuticals and vaccines in plants via the chloroplast genome." Biotechnology Journal. Sep. 2006. vol. 1 No. 10 pgs.
Arlen et al., Effective plague vaccination via oral delivery of plant cells expressing F1-V antigens in chloroplasts, Infect Immun., 2008, 76(8), 3640-50.
Daniell et al., The complete nucleotide sequence of the cassava (*Manihot esculenta*) chloroplast genome and the evolution of atpF in Malpighiales: RNA editing and multiple losses of a group II intron, Theor Appl Genet., 2008, 116(5) 723-37.
Chebolu et al., Stable expression of Gal/GalNAc lectin of Entamoeba histolytica in transgenic chloroplasts and immunogenicity in mice towards vaccine development for amoebiasis, Plant Biotechnol J., 2007, 5(2), 230-9.
Daniell et al., Transgene containment by maternal inheritance: effective or elusive? Proc Natl Acad Sci U S A, 2007, 104(17), 6879-80.
Molina et al., High-yield expression of a viral peptide animal vaccine in transgenic tobacco chloroplasts, Plant Biotechnol J., 2004, 2(2), 141-53.
Ruhlman et al., Expression of cholera toxin B-proinsulin fusion protein in lettuce and tobacco chloroplasts—oral administration protects against development of insulitis in non-obese diabetic mice, Plant Biotechnol J., 2007, 5(4), 495-510.

(Continued)

*Primary Examiner* — Anne Kubelik
(74) *Attorney, Agent, or Firm* — Howson & Howson, LLP; Kathleen D. Rigaut

(57) ABSTRACT

Disclosed herein are compositions for conferring oral tolerance in mammals to autoimmune disorders such as diabetes, as well as vectors and methods for plastid transformation of plants to produce a CTB-Pins protein for oral delivery. The invention also extends to the transformed plants, plant parts, and seeds and progeny thereof. The invention is applicable to plants edible without torrefying. Exemplified herein is the stable transformation of *Lactuca sativa* such that CTB-Pins is expressed.

10 Claims, 12 Drawing Sheets

(56) References Cited

OTHER PUBLICATIONS

Verma et al., Chloroplast vector systems for biotechnology applications, Plant Physiol., 2007, 145(4), 1129-43.
Daniell et al., Chloroplast genetic engineering, Biotechnol J., 2006, 1(1), 26-33.
Lee et al., Plastid transformation in the monocotyledonous cereal crop, rice (Oryza sativa) and transmission of transgenes to their progeny, Mol Cells., 2006, 21(3), 401-10.
Limaye et al., Receptor-mediated oral delivery of a bioencapsulated green fluorescent protein expressed in transgenic chloroplasts into the mouse circulatory system, FASEB J., 2006, 20(7), 959-61.
Daniell et al., Breakthrough in chloroplast genetic engineering of agronomically important crops, Trends Biotechnol., 2005, 23(5), 238-45.
Koya et al., Plant-based vaccine: mice immunized with chloroplast-derived anthrax protective antigen survive anthrax lethal toxin challenge, Infect Immun., 2005, 73(12), 8266-74.
Quesada-Vargas et al., Characterization of heterologous multigene operons in transgenic chloroplasts: transcription, processing, and translation, Plant Physiol., 2005, 138(3), 1746-62.
Kumar et al., Stable transformation of the cotton plastid genome and maternal inheritance of transgenes, Plant Mol Biol., 2004, 56(2), 203-16.
Kumar et al., Plastid-expressed betaine aldehyde dehydrogenase gene in carrot cultured cells, roots, and leaves confers enhanced salt tolerance, Plant Physiol., 2004, 136(1), 2843-54.

Watson et al., Expression of Bacillus anthracis protective antigen in transgenic chloroplasts of tobacco, a non-food/feed crop, Vaccine, 2004, 22(31-32), 4374-84.
Daniell et al., Multigene engineering: dawn of an exciting new era in biotechnology, Curr Opin Biotechnol., 2002, 13 (2), 136-41.
Daniell et al., Milestones in chloroplast genetic engineering: an environmentally friendly era in biotechnology, Trends Plant Sci., 2002, 7(2), 84-91.
Bergerot et al., A cholera toxoid-insulin conjugate as an oral vaccine against spontaneous autoimmune diabetes, Proc Natl Acad Sci USA, 1997, 94, 4610-4614.
Harrison et al., Insulin induces regulatory CD8 T Cells that prevent murine insulin-dependent diabetes. J Exp Med, 1996, 184, 2167-2174.
Weiner et al., Oral tolerance, Immunol Rev, 2005, 206, 232-59.
Li et al., Cholera toxin B subunit binding to an antigen-presenting cell directly co-stimulates cytokine production from a T cell clone, Int Immunol, 1999, 8, 1849-1856.
Limaye et al., Receptor mediated oral delivery green fluorescent protein expressed in transgenic chloroplasts into the mouse circulatory system, FASEB J, 2006, 20, 959-961.
Sun et al., Cholera toxin B subunit: an efficient transmucosal carrier-delivery system for induction of peripheral immunological tolerance, Proc Natl Acad Sci USA, 1994, 91, 10795-10799.
Posgai, A. L. et al. Plant-based vaccines for oral delivery of type 1 diabetes-related autoantigens: Evaluating oral tolerance mechanisms and disease prevention in NOD mice. Sci. Rep. 7, 42372; doi: 10.1038/srep42372 (2017).

* cited by examiner

CHLOROPLASTS ENGINEERED TO EXPRESS PHARMACEUTICAL PROTEINS IN EDIBLE PLANTS

RELATED APPLICATIONS

This application claims priority to U.S. Ser. No. 60/909,158 filed Mar. 30, 2007, which is incorporated herein in its entirety by reference.

GOVERNMENT RIGHTS

This invention was made with government support under grant no. GM063879 awarded by the National Institute of Health and under grant no. 58-3611-2-106 awarded by the United States Departments of Agriculture/Agricultural Research Service. The government has certain rights in the invention.

BACKGROUND

Diabetes is a disease in which the body does not produce or properly utilize insulin. Type 1 diabetes results from the autoimmune destruction of insulin-producing cells. The major destruction of β-cells occurs predominantly from autoreactive T-cytotoxic cells (Nagata et al., 1994) and T-helper 1 cells (Ploix et al, 1999) reactive to β-cell autoantigens such as insulin. In 2002, the American Diabetes Association estimated that 18.2 million people in the United States, or 6.3% of the total population, have diabetes, with more than $120 billion in treatment costs each year. In 2002, diabetes was the sixth leading cause of death in the U.S. contributing to 213,062 deaths. The only currently accepted form of treatment is the administration of recombinant insulin, which serves to temporarily replace the missing insulin in diabetic patients. Therefore, it is essential to find a prevention and cure for this dreadful disease.

DETAILED DESCRIPTION

Figure 1A:
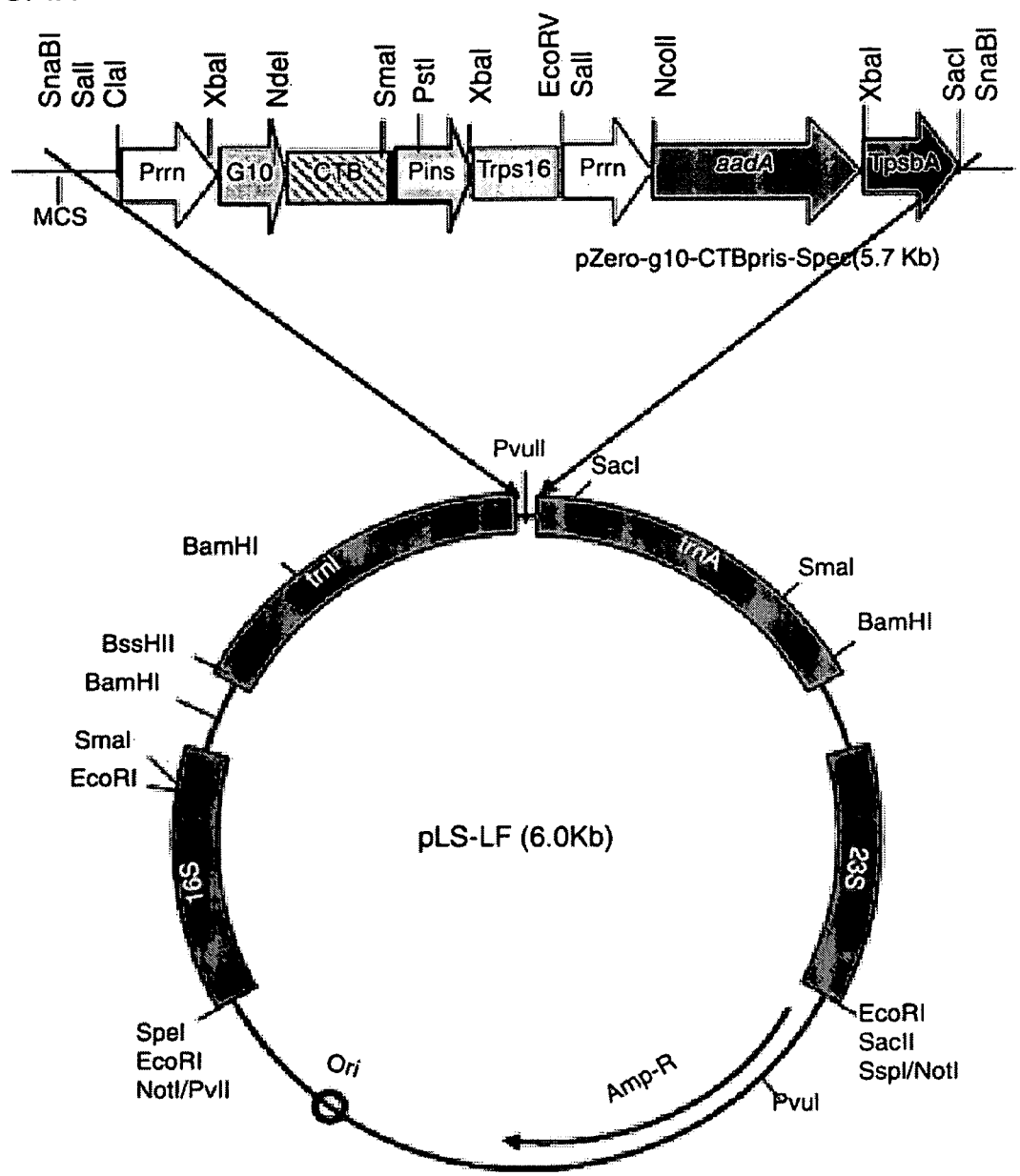
FIG. 1: Regeneration and Southern analysis of CTB-Pins lettuce transformants. Schematic diagrams of lettuce transformation vector and integration cassette (FIG. 1A), integration site and resulting tranplastome. Solid lines indicate sizes of integration cassette (2.4 kb), expected fragment for wild type (3.75 kb) and transformed (6.15 kb) genomes in Southern analysis; dashed line indicate probe hybridization sites (FIG. 1B). Southern analysis of second regenerants; L100 and L101 are independent transplastomic lines, WT is untransformed (FIG. 1C). Primary regeneration in lettuce without formation of callus (FIG. 1D).
Figure 1B:
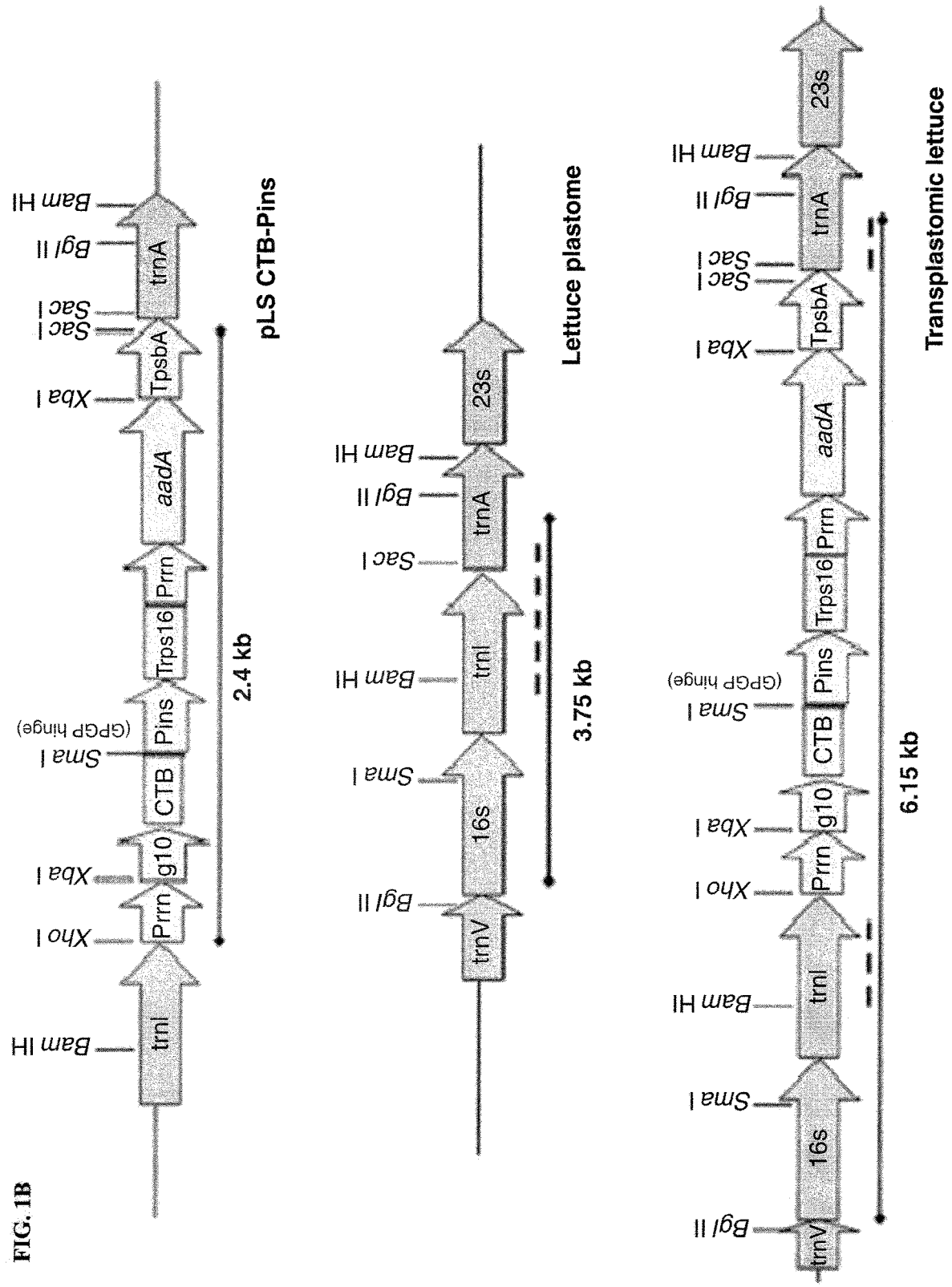

Embodiments of the present invention pertain to the novel expression of therapeutic proteins in chloroplasts of edible plants. Some plants such as potato contain components that make them not suitable for eating raw, but which are edible upon further processing, such as by cooking. In more specific embodiments, the present invention pertains to plant cells from plants edible without cooking, wherein the plant cells comprise chloroplasts transformed to express therapeutic proteins. In a one embodiment, a CTB-proinsulin (CTB-Pins) conjugate is expressed in the chloroplasts of *Lactuca sativa* representing the first demonstration of a therapeutic protein being expressed in chloroplasts of an edible plant. According to another embodiment, the invention is directed to a method of retarding the development or treating of diabetes in a subject in need thereof. The method involves administering to to the subject a composition comprising a CTB-Pins polypeptide and a plant remnant from a plant edible without cooking.

The term "a plant edible without cooking" refers to a plant that is edible, i.e., edible without the need to be subjected to heat exceeding 120 deg F. for more than 5 min. Examples of such plants include, but are not limited to, *Lactuca sativa* (lettuce), apple, berries such as strawberries and raspberries, citrus fruits, tomato, banana, carrot, celery, cauliflower; broccoli, collard greens, cucumber, muskmelon, watermelon, pepper, pear, grape, peach, radish and kale. In a specific embodiment, the edible plant is *Lactuca sativa*.

Edible plants that require cooking or some other processing are not excluded from the teachings herein.

A plant remnant may include one or more molecules (such as, but not limited to, proteins and fragments thereof, minerals, nucleotides and fragments thereof, plant structural components, etc.) derived from the plant in which the protein of interest was expressed. Accordingly, a composition pertaining to whole plant material (e.g., whole or portions of plant leafs, stems, fruit, etc.) or crude plant extract would certainly contain a high concentration of plant remnants, as well as a composition comprising purified protein of interest that has one or more detectable plant remnants. In a specific embodiment, the plant remnant is rubisco.

In another embodiment, the invention pertains to an administratable composition for retarding the development of or treating diabetes. The composition comprises a therapeutically-effective amount of CTB-Pins protein having been expressed by a plant and a plant remnant.

According to a further embodiment, the invention pertains to a stable plastid transformation and expression vector which comprises an expression cassette comprising, as operably linked components in the 5' to the 3' direction of translation, a promoter operative in said plastid, a selectable marker sequence, a heterologous polynucleotide sequence coding for comprising at least 70% identity to a CTB-Pins protein, transcription termination functional in said plastid, and flanking each side of the expression cassette, flanking DNA sequences which are homologous to a DNA sequence of the target plastid genome, whereby stable integration of the heterologous coding sequence into the plastid genome of the target plant is facilitated through homologous recombination of the flanking sequence with the homologous sequences in the target plastid genome.

It is the inventor's belief that biopharmaceutical proteins expressed in plant cells should reduce their cost of production. Transformation of plant nuclear genomes has led to the expression of a number clinically important molecules in cell culture, organized tissue culture and in whole plants (Rigano and Walmsley, 2005). Common crop species such as potatoes, rice and tomatoes have been engineered to express many therapeutic proteins via the nuclear genomes of these plants (Ma et al., 2003).

One of the major limitations has been the ability in these systems to accumulate sufficient levels of protein either for purification or for oral delivery in minimally processed plant tissues. Integration of transgenes via the nuclear genome may have other disadvantages including transgene containment, gene silencing, and position effect. The chloroplast genetic engineering approach overcomes concerns of transgene containment (Daniell, 2002), gene silencing and position effect (De Cosa et al, 2001; Lee et al., 2003), pleiotropic effects (Daniell et al., 2001; Lee et al., 2003), and presence of antibiotic resistant genes or vector sequences in transformed genomes (Daniell et al., 2004a, 2004b, 2005a, 2005b, Grevich and Daniell 2005). Multigene engineering is possible with chloroplast transformation due to its prokaryotic nature (DeCosa et al., 2001; Quesada-Vargas et al., 2005). Several vaccine antigens have been expressed via the chloroplast genome against bacterial, viral and protozoan pathogens including the Cholera toxin B-subunit (Daniell et al., 2001), anthrax protective antigen (Watson et al., 2004; Koya et al., 2005), the C-terminus of *Clostridium tetani* (Tregoning et al., 2003), the 2L21 peptide from the Canine Parvovirus (Molina et al, 2004), rotavirus VP6 protein (Birch-Machin et al, 2004) and the GAL/GALNAc lectin of *Entamoeba histolytica* (Chebolu and Daniell, 2007).

In addition to its use for the hyper-expression of vaccine antigens, transgenic chloroplasts have been used by the inventor for the production of valuable therapeutic proteins, such as human elastin-derived polymers for various biomedical applications (Guda et al., 2000); human serum albumin (Fernandez-San Millan et al, 2003); magainin, a broad spectrum topical agent, systemic antibiotic, wound healing stimulant and a potential anticancer agent (DeGray et al, 2001); various interferon a proteins (Daniell et al, 2004a, 2005a; Arlen et al., 2007) and insulin-like growth factor 1 (Daniell et al., 2005a). Several other laboratories have expressed other therapeutic proteins, including human somatotropin (Staub et al, 2000) and interferon γ-GUS fusion proteins (Leelavathi and Reddy 2003) in transgenic chloroplasts. The successful expression and assembly of complex multi-subunit proteins exemplified supports the theory that chloroplasts may be able to accomplish proper folding and disulfide bond formation, resulting in fully functional proteins (Kamarajugadda and Daniell, 2006).

Oral delivery of biopharmaceutical proteins expressed in plant cells should reduce costs associated with purification, processing, cold storage, transportation and delivery. However, poor intestinal absorption of intact proteins has been a major challenge. To overcome this limitation, the inventor investigated the concept of receptor-mediated oral delivery of transgenic proteins (Limaye et al, 2006). The B-subunit of the toxin from *Vibrio cholerae* (CTB) is recognized as being among the most potent of mucosal adjuvants (Holmgren et al., 2005). CTB and green fluorescent protein (CTB-GFP), separated by a furin cleavage site, was expressed via the tobacco chloroplast genome. Following oral administration of CTB-GFP expressing leaf material to mice, GFP was observed in the mice intestinal mucosa, liver and spleen in fluorescence and immunohistochemical studies, while CTB remained in the intestinal cell (Limaye et al., 2006).

Methods, vectors, and compositions for transforming plants and plant cells are taught for example in WO 01/72959; WO 03/057834; and WO 04/005467. WO 01/64023 discusses use of marker free gene constructs.

Proteins expressed in accord with certain embodiments taught herein may be used in vivo by administration to a subject, human or animal in a variety of ways. The pharmaceutical compositions may be administered orally or parenterally, i.e., subcutaneously, intramuscularly or intravenously, though oral administration is preferred.

Oral compositions produced by embodiments of the present invention can be administered by the consumption of the foodstuff that has been manufactured with the transgenic plant producing the plastid derived therapeutic protein. The edible part of the plant, or portion thereof, is used as a dietary component. The therapeutic compositions can be formulated in a classical manner using solid or liquid vehicles, diluents and additives appropriate to the desired mode of administration. Orally, the composition can be administered in the form of tablets, capsules, granules, powders and the like with at least one vehicle, e.g., starch, calcium carbonate, sucrose, lactose, gelatin, etc. The preparation may also be emulsified. The active immunogenic ingredient is often mixed with excipients which are pharmaceutically acceptable and compatible with the active ingredient. Suitable excipients are, e.g., water, saline, dextrose, glycerol, ethanol or the like and combination thereof. In addition, if desired, the compositions may contain minor amounts of auxiliary substances such as wetting or emulsifying agents, pH buffering agents, or adjuvants. In a preferred embodiment the edible plant, juice, grain, leaves, tubers, stems, seeds, roots or other plant parts of the pharmaceutical producing transgenic plant is ingested by a human or an animal thus providing a very inexpensive means of treatment of or immunization against disease.

In a specific embodiment, plant material (e.g. lettuce material) comprising chloroplasts capable of expressing CTB-Pins is homogenized and encapsulated. In one specific embodiment, an extract of the lettuce material is encapsulated. In an alternative embodiment, the lettuce material is powderized before encapsulation.

In alternative embodiments, the compositions may be provided with the juice of the transgenic plants for the convenience of administration. For said purpose, the plants to be transformed are preferably selected from the edible plants consisting of tomato, carrot and apple, among others, which are consumed usually in the form of juice.

According to another embodiment, the subject invention pertains to a transformed chloroplast genome that has been transformed with a vector comprising a heterologous gene that expresses a peptide as disclosed herein.

Of particular present interest is a transformed chloroplast genome that has been transformed with a vector comprising a heterologous gene that expresses a CTB-Pins polypeptide. In a related embodiment, the subject invention pertains to a plant comprising at least one cell transformed to express a peptide as disclosed herein.

Reference to specific polypeptide sequences herein (such as but not limited to, CTB and proinsulin (or those listed in Table 1 below) relate to the full length amino acid sequences as well as at least 12, 15, 25, 50, 75, 100, 125, 150, 175, 200, 225, 250 or 265 contiguous amino acids selected from such amino acid sequences, or biologically active variants thereof.

Variants which are biologically active, refer to those, in the case of oral tolerance, that activate T-cells and/or induce a Th2 cell response, characterized by the upregulation of immunosuppressive cytokines (such as IL10 and IL4) and serum antibodies (such as IgG1), or, in the case of desiring the native function of the protein, is a variant which maintains the native function of the protein. Preferably, naturally or non-naturally occurring polypeptide variants have amino acid sequences which are at least about 55, 60, 65, or 70, preferably about 75, 80, 85, 90, 96, 96, or 98% identical to the full-length amino acid sequence or a fragment thereof. Percent identity between a putative polypeptide variant and a full length amino acid sequence is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of polypeptide can be found using computer programs well known in the art, such as DNASTAR software. Whether an amino acid change results in a biologically active LecA polypeptide can readily be determined by assaying for native activity, as described for example, in the specific Examples, below.

Reference to genetic sequences herein refers to single- or double-stranded nucleic acid sequences and comprises a coding sequence or the complement of a coding sequence for polypeptide of interest. Degenerate nucleic acid sequences encoding polypeptides, as well as homologous nucleotide sequences which are at least about 50, 55, 60, 65, 60, preferably about 75, 90, 96, or 98% identical to the cDNA may be used in accordance with the teachings herein polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of nucleic acid sequences which encode biologically active polypeptides also are useful polynucleotides.

Variants and homologs of the nucleic acid sequences described above also are useful nucleic acid sequences. Typically, homologous polynucleotide sequences can be identified by hybridization of candidate polynucleotides to known polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of polynucleotides referred to herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81,123 (1973). Nucleotide sequences which hybridize to polynucleotides of interest, or their complements following stringent hybridization and/or wash conditions also are also useful polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ of a hybrid between a polynucleotide of interest or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\% G+C) - 0.63(\% \text{formamide}) - 600/1,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Relevant articles on genetic sequences is provided: proinsulin (Brousseau et al., Gene, 1982 March; 17(3):279-89; Narrang et al, *Can J Biochem Cell Biol.* 1984 April; 62(4): 209-16; and Georges et al, *Gene* 27 (2), 201-211 (1984); and CTB (Shi et al, Sheng Wu Hua Hsueh Tsa Chih 9 (No. 4), 395-399 (1993).

According to another embodiment, the invention pertains to a method of producing a CTB-Pins containing composition, the method including obtaining a stably transformed *Lactuca sativa* plant which includes a plastid stably transformed with an expression vector which has an expression cassette having, as operably linked components in the 5' to the 3' direction of translation, a promoter operative in a plastid, a selectable marker sequence, a heterologous polynucleotide sequence coding for comprising at least 70% identity to a CTB-Pins protein, transcription termination functional in said plastid, and flanking each side of the expression cassette, flanking DNA sequences which are homologous to a DNA sequence of the target plastid genome, whereby stable integration of the heterologous coding sequence into the plastid genome of the target *Lactuca sativa* plant is facilitated through homologous recombination of the flanking sequence with the homologous sequences in the target plastid genome; and homogenizing material of said stably transformed *Lactuca sativa* plant to produce homogenized material.

In addition to a CTB-Pins protein, *Lactuca sativa* chloroplasts can be transformed to express pharmaceutical proteins of interest. Provided in Table 1 is a list of examples of other proteins that may be expressed in *Lactuca sativa* and a cross-reference to related patents or patent pubs.

TABLE 1

| Pharmaceutical Proteins | Related Patents or Patent Pubs |
| --- | --- |
| CTB-conjugated proteins in general | WO 2007/053183 and U.S. Patent Pub 20060117412 |
| CTB-NSP4 | WO 2007/053183 |
| CTB-GFP | WO 2007/053183 |
| NS3 | WO 2007/053183 |
| IFNα5 | WO 2007/053183 |
| Protective antigen | WO 2007/053183 |
| LecA | WO 2007/053182 |
| Human Igf-1 | U.S. Patent Pub. 20070124838 |
| Human serum albumin | U.S. Patent Pub 2007/0067862 |
| interferon | U.S. Patent Pub 2003/0204864 |
| Hepatitis B surface antigen | U.S. Pat. No. 7,129,391 and 5,914,123 |

According to another embodiment, the subject invention pertains to a pharmaceutical protein sample bioencapsulated in choroplasts of a plant cell. The chloroplasts have been modified to express the pharmaceutical protein. Protein is produced in the modified chloroplasts and barring rupture or some other disruptive stimulus, the protein is pooled and stored in the chloroplast. Thus the chloroplast acts as a protective encapsulation of the protein sample Example 1: Expression of Cholera Toxin B Subunit-Proinsulin Fusion Protein in Transgenic *Lactuca Sativa* Chloroplasts as a Treatment Against Development of Type-1 Autoimmune Diabetes Studies by the inventor support the proposition that there are advantages to plastid expression. Transformation of plastids in non-green tissue has been achieved, especially in edible parts of carrot, providing access to several new potential platforms for pharmaceutical production (Daniell et al., 2005b; Kumar et al, 2004a, 2004b). But in terms of minimally processed orally delivered vegetative biomass, the inventors postulate that expression of therapeutic proteins in chloroplasts must be successfully demonstrated in edible crop plant systems. Although recently two labs report stable plastid transformation in lettuce, expression of therapeutic proteins has been unsuccessful (Kanamoto et al., 2006; Lelivelt et al., 2005), *Lactuca sativa* (lettuce) was nonetheless pursued for plastid expression of therapeutic proteins.

The non-obese diabetic (NOD) mouse is a useful animal model for research in human diabetes (Homann et al., 1999). These mice show signs of insulitis due to lymphocytic infiltration of the endocrine part of the pancreas, which leads to decreased production of insulin and increased blood sugar with its consequent pathologies.

Results

Vector Construction of pLD-5'UTR-CTB-Human Proinsulin

Figure 2A:
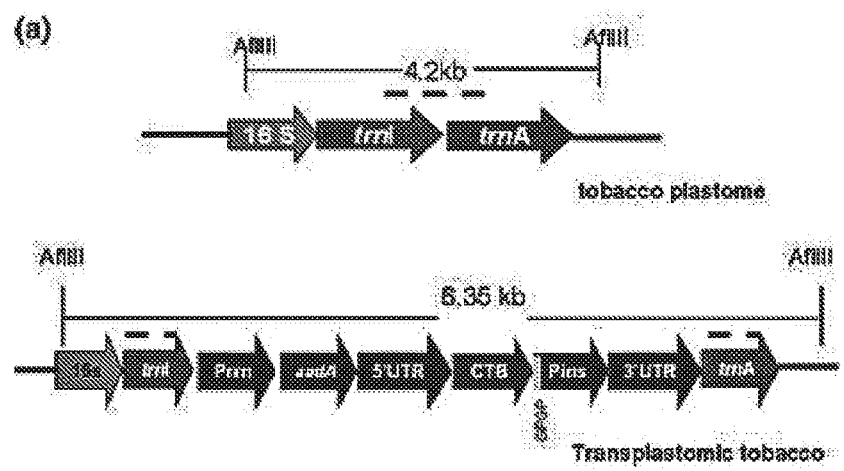
FIG. 2: Southern analysis of CTB-Pins tobacco transformants. Schematic representation of expected results in Southern analysis; solid lines indicate expected fragment for wild type (4.2 kb) and transformed (6.35 kb) genomes; dashed line indicates probe hybridization sites (A). Southern analysis of second regenerants; 5CP lines 13, 14, M, O and P were derived from independent transformation events; WT is untransformed (B).

The CTB-Pins fusion gene was inserted into the chloroplast transformation vector pLD-ctv as previously described (Daniell et al., 2004b). The 5CP construct was expressed under the control of the psbA 5'UTR/promoter in order to achieve hyper-expression as previously demonstrated for other transgenes (Daniell et al., 2004b). To prevent steric hindrance a GPGP hinge was introduced between the fusion elements (Arakawa et al., 1998). The 3'UTR located at the 3' end of the introduced gene confers transcript stability (Stem and Gruissem, 1987, FIG. 2A).

*Lactuca sativa* long flanking plastid transformation vector (pLS-LF, FIG. 1A) was constructed using primers derived from regions of known conservation in the *N. tabacum* plastome to amplify cognate sequences from the *L. sativa* plastome. The full length genes for plastid tRNA-Ile (1020 bp) tRNA-Ala (887 bp) were amplified and cloned. The unique PvuII site was used to insert transformation cassettes into the intergenic spacer region between the tRNAs. Long flanking sequences encoding portions of the 16S (810 bp) and 23S (974 bp) ribosomal RNA subunits were included to enhance homologous recombination between the vector and the host plastome. The tobacco native plastid ribosomal operon promoter (Prrn) and 3' UTRs (psbA and rps 16) were used to drive expression of AadA from GGAGG ribosome binding site and CTB-Pins from the 5' translation control element of bacteriophage T7 gene10 (FIG. 1A). Following assembly of pLS-LF-CTB-Pins plasmids were isolated from spectinomycin resistant cultures and correct orientation was confirmed by SacI digest.

Transformation and Regeneration of Transplastomic Plants

Bombardment of 10 tobacco leaves resulted in 56 independent transformation events, 40 of which were subjected to three rounds of selection, two on RMOP and one on MS0 medium which contained 500 mg $L^{-1}$ spectinomycin and integration of the transgene cassette was confirmed by PCR.

Figure 1C:
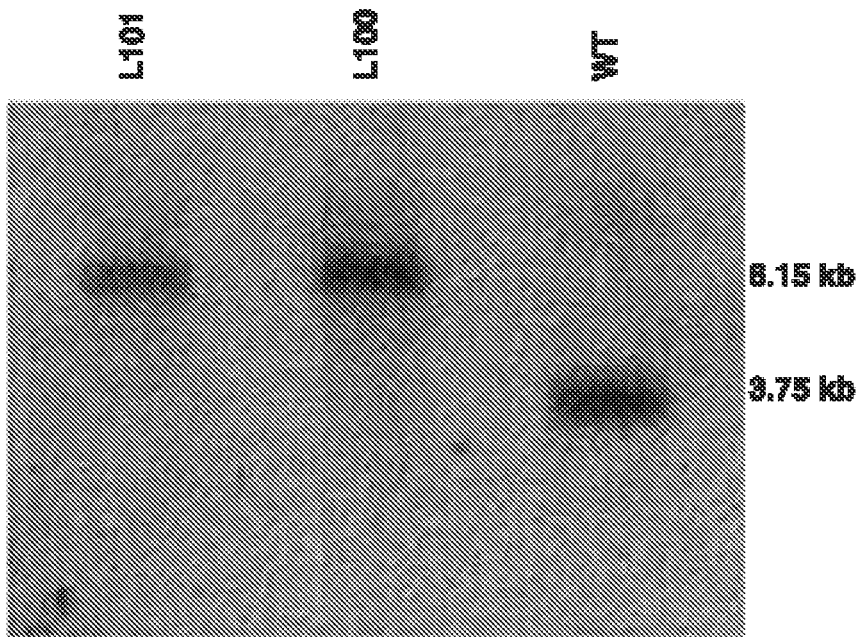
Figure 1D:
Figure 3:
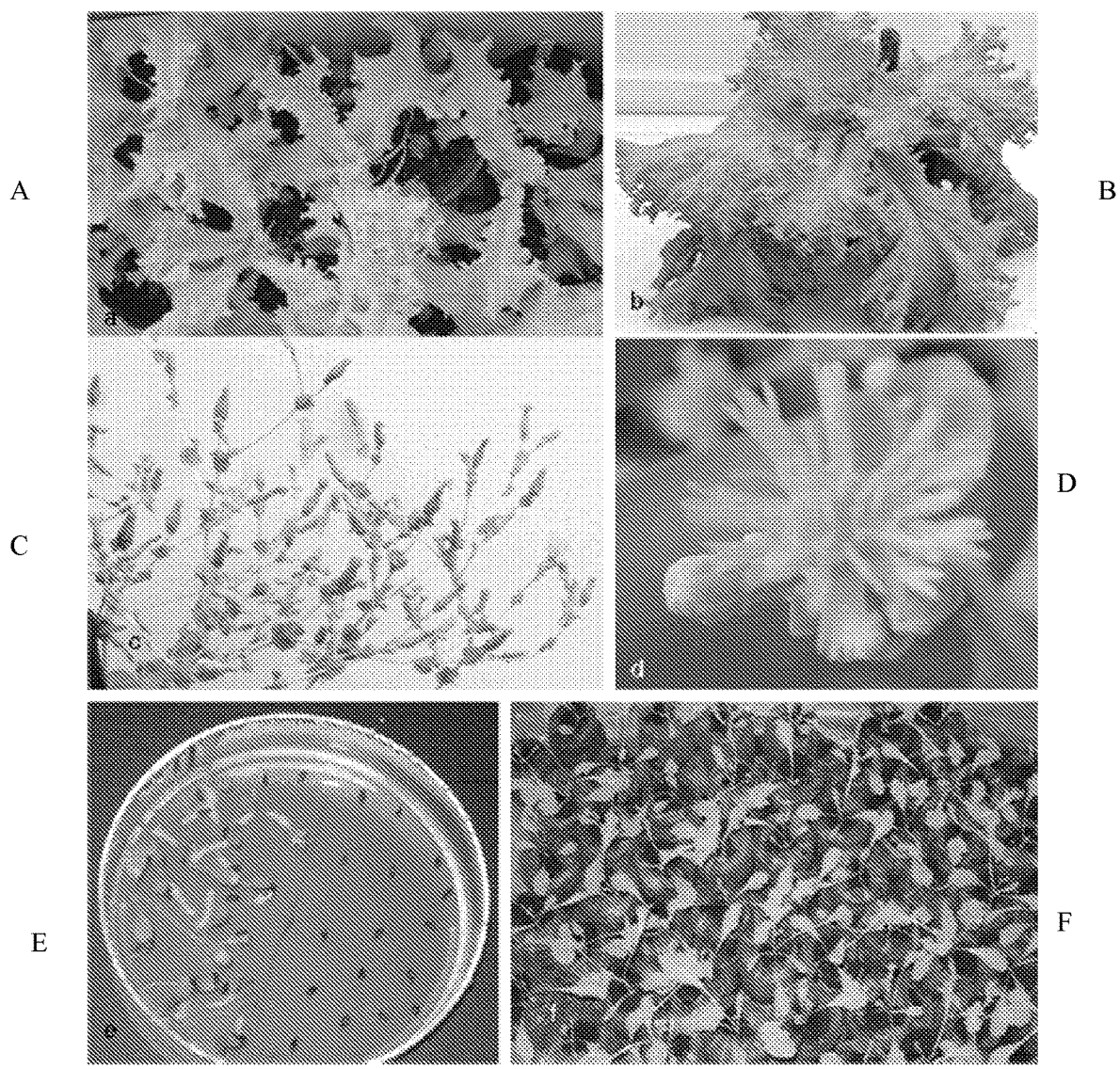
FIG. 3: Production of transplastomic *L. sativa* and confirmation of maternal inheritance. Lettuce plants propogated by rooting of nodal cuttings were transferred to soil in the greenhouse (A). Plants matured with no apparent aberrant phenotype (B) and produced normal inflorescence (C). Flowers heads opened (D), and seeds were harvested. T1 seeds were plated on half strength MS with 50 mg $L^{-1}$ spectinomycin along with wild type seed (E). TI plants flourished and were transferred to the greenhouse (F).

Bombardment of 60 lettuce leaves resulted in two independent transformation events (lines L100 and L101) identified as green shoots arising directly from completely bleached tissue on LR medium with 50 mg $L^{-1}$ spectinomycin (FIG. 1D). It should be noted that no callus was formed prior to initiation of shoots from leaf explants. Following an additional round of selective regeneration, a progenitor for each line was rooted in MS with spectinomycin (50 mg $L^{-1}$) and multiplied by clonal propagation. Clones were transferred to soil (FIG. 3A) and moved to the greenhouse where they matured (FIG. 3B), bolted, produced normal panicles (FIG. 3C) and inflorescence with disc flowers (FIG. 3D). Pappus-bearing achenes (seeds) were harvested. Lettuce seeds (T1) were sterilized and germinated on spectinomycin media (50 mg $L^{-1}$) along with WT seeds (FIG. 3E). T1 seeds germinated and grew into uniformly green plants (FIG. 3F). The absence of Mendelian segregation of transgenes indicated that they are maternally inherited to progeny. Most wild type seeds failed to germinate on spectinomycin media. Of wild type 30 seeds plated, 6 reached radicle emergence but hypocotyl emergence was not observed and none developed into seedlings.

Analysis of the Transgenic Chloroplast Genome Confirms Homoplasmy

Figure 2B:
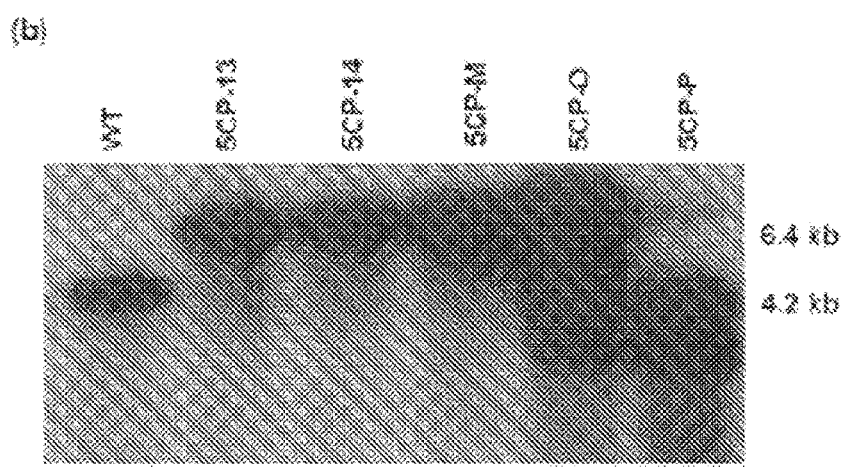

Chloroplast transgenic lines were examined by Southern analysis in order to confirm site-specific integration and to determine whether they were homoplasmic or heteroplasmic. Homoplasmy is achieved when all the copies of the genome within the chloroplast have stably integrated transgenes. For tobacco the gene-specific probe (CTB-Pins) taken from the pLD-5CP vector by MfeI/NotI digestion hybridized to a single 6.4 kb fragment in transgenics but not to any wild-type plant DNA fragment (data not shown). The flanking sequence probe contained regions of the trnI and trnA genes. In most of the transgenic lines only the 6.4 kb fragment was seen when hybridized with this probe (FIG. 2B), indicating that homoplasmy was achieved within limits of detection by Southern blot.

For confirmation of homoplasmy in lettuce transgenic lines labeled flanking sequence probe (1.3 kb) was hybridized to BglII digested genomic DNA. Hybridization pattern shows only the expected 3.75 kb fragment in wild type sample and only the expected 6.15 kb fragment in lettuce transformants after second regeneration (FIG. 1C). W Southern blotting with genomic DNA samples from the primary regenerants was conducted. While the L100 line demonstrated heteroplasmy, with both wild type and transformed fragments hybridizing with the probe, primary regenerant L101 appears to be homoplasmic (data not shown). Previous studies by the inventor with tobacco have demonstrated that homoplasmy can indeed be achieved in the first round of selection (Guda et al. 2000) because the flanking sequence contained an origin of replication (thereby providing more templates for integration). As the lettuce transformation vector includes full length lettuce trnI gene, which probably contains the OriA, it is not unreasonable to find this phenomenon in lettuce plastid transformants as well.

CTB-Proinsulin Accumulation and Pentamer Assembly in Transgenic Chloroplasts

Figure 4A:
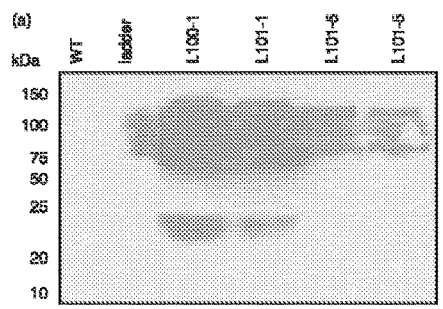
FIG. 4: Protein analyses. Western blots prepared from WT and transplastomic lettuce and tobacco were probed with human proinsulin mAb. Total protein (~20 μg) extracted from lettuce leaves was loaded into wells for each sample. In lane 6, L101-5, ~10 μg tsp was loaded (A). Total protein (~10 μg) extracted from tobacco leaves was loaded into wells (B). CTB-Pins in plants samples was detected by polyclonal anti-CTB and quantified by comparison to known quantities of CTB standard. Lanes 1-3, bacterial CTB (25, 50, 100 ng); Transplastomic tobacco lines 5CP-13, 5CP-13, 5CP-M (~6 μg tsp each lane); transplastomic lettuce lines L-100, L-101 (~36 μg tsp each lane), (C). Plot of *integrated density values (IDV) for quantitative analysis from standard curve. Broken line=data points, solid is the trendline (D). Estimation of CTB-Pins in tobacco and lettuce leaves by spot densitometry CTB immunoblots (E). Tobacco and lettuce transformants were assayed for GM1 binding. 5CP, CTB:Pins tobacco; L101 & L101, CTB-Pins lettuce; BSA, negative control (F).
Figure 4B:
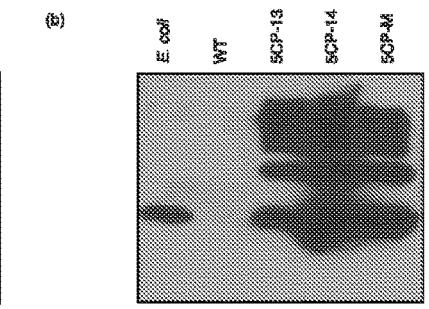
Figure 4C:
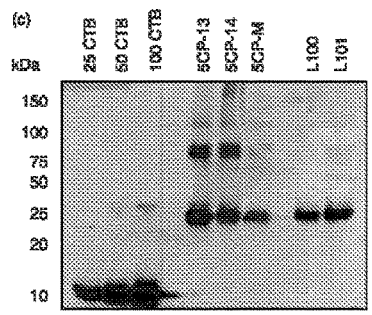
Figure 4D:
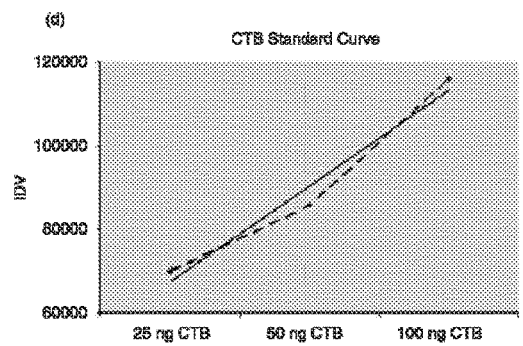
Figure 4E:
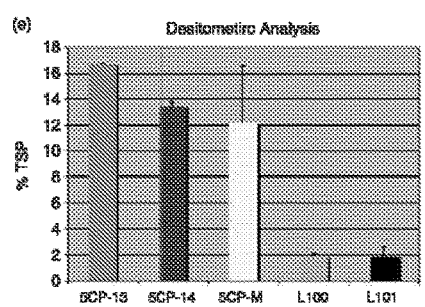
Figure 4F:
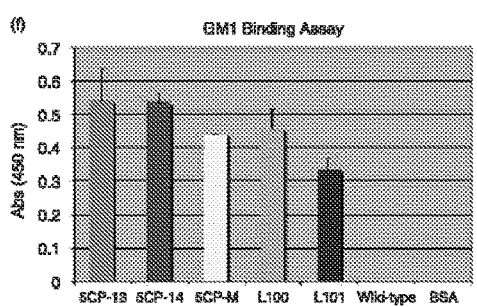

Immunoblots probed with the human proinsulin mAb showed the presence of ~22 kDa fusion protein in the chloroplast transgenic lines. The formation of dimers, trimers, tetramers, and pentamers of the CTB-Pins fusion protein was also observed (FIGS. 4A&B). A similar banding pattern was observed by immunodetection with CTB polyclonal antibody (FIG. 4C). Quantification of the fusion protein on western blots was performed by comparing plant samples with known quantities of purified CTB and analyzing them by spot densitometry. Linearity of the standard curve was achieved using 25 ng, 50 ng and 100 ng facilitating estimation of CTB expression in samples in the same blot (FIG. 4D). The three tobacco transgenic lines were found to contain up to 178.2 μg, 126.7 ρg and 139.1 μg of CTB-proinsulin per 100 mg of leaf tissue, approximately 16% of tsp (FIG. 4E). Such variation could be due to the use of fresh versus frozen plant material for these assays or differences in sample preparation or growth conditions. Lettuce lines L100 and L101 accumulated up to 13.6 and 15.3 μg per 100 mg of leaf tissue, approximately 2.02 and 2.43% tsp respectively. The $GM_1$ binding assay demonstrated that pentameric structures of CTB-Pins were formed (FIG. 4F). This assay confirmed the correct folding and disulfide bond formation of CTB pentamers within transgenic chloroplasts since only the pentameric structure of CTB has the ability to bind to the $GM_1$ receptor (Merritt et al., 1994).

The expression level of CTB-Pins in tobacco or lettuce plants was unable to be established via ELISA. The highest absorbance values were observed in the GM1 binding assay from samples extracted under reducing conditions. While reduction of disulfide bonds would be expected to abrogate the ability of the fusion protein to associate with the plate-bound receptor in pentameric form (Ludwig et al., 1985; Dertzbaugh and Cox, 1998), plant extracts prepared in western extraction buffer (14 mM β-me) or with molar excess of dithiolthreitol (0.5 M DTT) clearly facilitated GM1 binding as indicated by elevated absorbance readings. The potential for protein aggregation to occur in plant extracts increases with the concentration of the protein in question. Together CTB monomers and the proinsulin molecule contain several cysteine residues through which disulfide bonds form, both intra- and intermolecular in nature. It was interpreted that aggregation of the CTB-proinsulin fusion confounded efforts to execute quantitative ELISAs.

Lymphocytic Infiltration of the Endocrine Part of Pancreas (Insulitis)

Insulitis is characterized by lymphocytic infiltration of the pancreatic islets, which leads to their destruction, including the insulin producing beta cells. Pancreata was obtained from twelve week old NOD mice from the different treatment groups to assess the degree of insulitis.

Figure 5A:
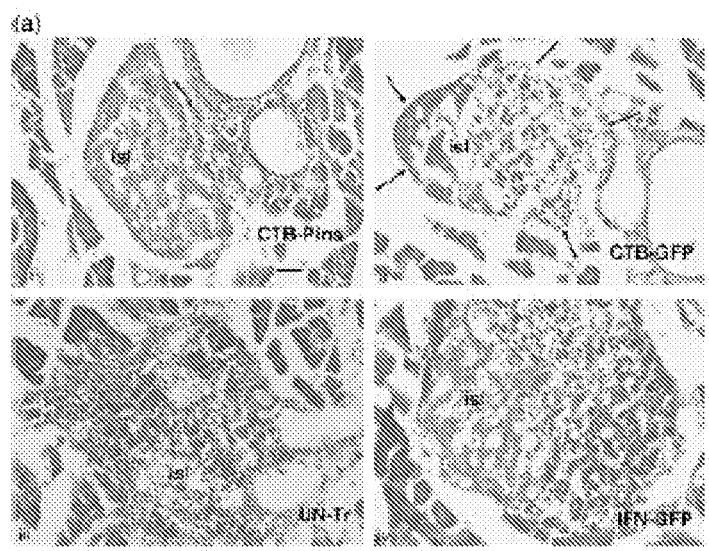
FIG. 5: Histochemical staining of pancreatic sections. A) Haematoxylin & Eosin staining of a section of the pancreas (showing an islet: isl) of a mouse gavaged with CTB-Pins for 7 weeks (n=7); scale bar=50 μm (a). Lymphocytes are seen outside the islet (arrow in A, frame a). Arrows in B indicate the borders of an islet in the pancreas of a mouse gavaged with CTB-GFP (n=5; control group). Blue dots show lymphocytic infiltration of the islet (b). A large islet with severe lymphocytic infiltration in a mouse gavaged with untransformed (UN-Tr; n=3) plant leaf material (c). Severe lymphocytic infiltration in a mouse gavaged with IFN-GFP (d; n=5). B) Scoring (S) of the degree of insulitis according to the severity of the lymphocytic infiltration of the pancreas Langerhans islets. Score 1 indicates no or pre-islet infiltration, minimal infiltrations were scored 2, moderate infiltrations were scored 3 and severe infiltrations were scored 4. When more than 80% of the islands were infiltrated, the score was 5. All sections were scored blindly. C) Graphic representation of insulitis scoring Untransformed (UN-Tr) plant, IFN-GFP, or CTB-GFP plant treated groups; bars represent standard deviation (*P<0.05). 'n' designates the number of animals in each treatment group.
Figure 5B:
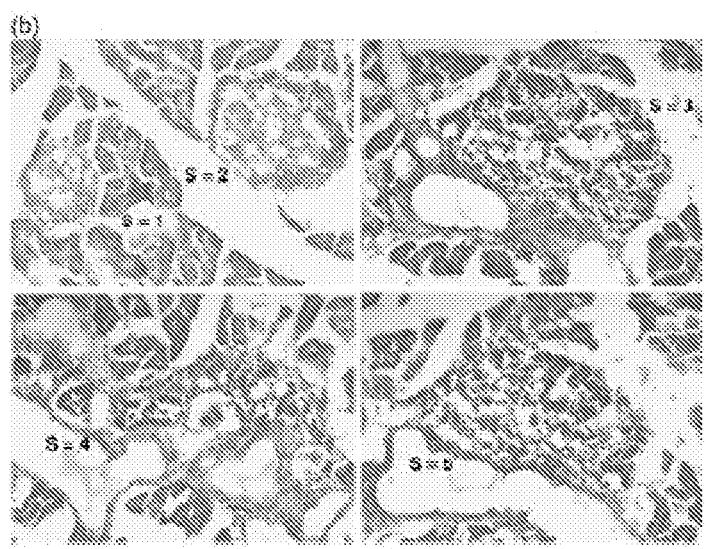
Figure 5C:
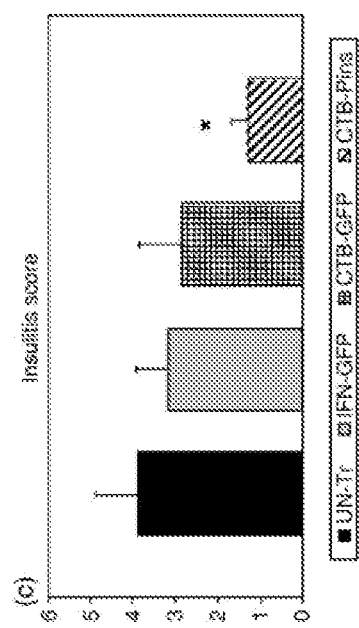

To quantify and compare the insulitis of each treatment group, representative sections were prepared from each treatment group and cellular infiltrations were scored blindly. Fifty sections per animal were analyzed and the average score indicated that the pancreata from NOD mice administered CTB-Pins had minimal cellular infiltration, and this reduction in cellular infiltration is significantly less than all other treatment groups (FIG. 5A-C).

Figure 6:
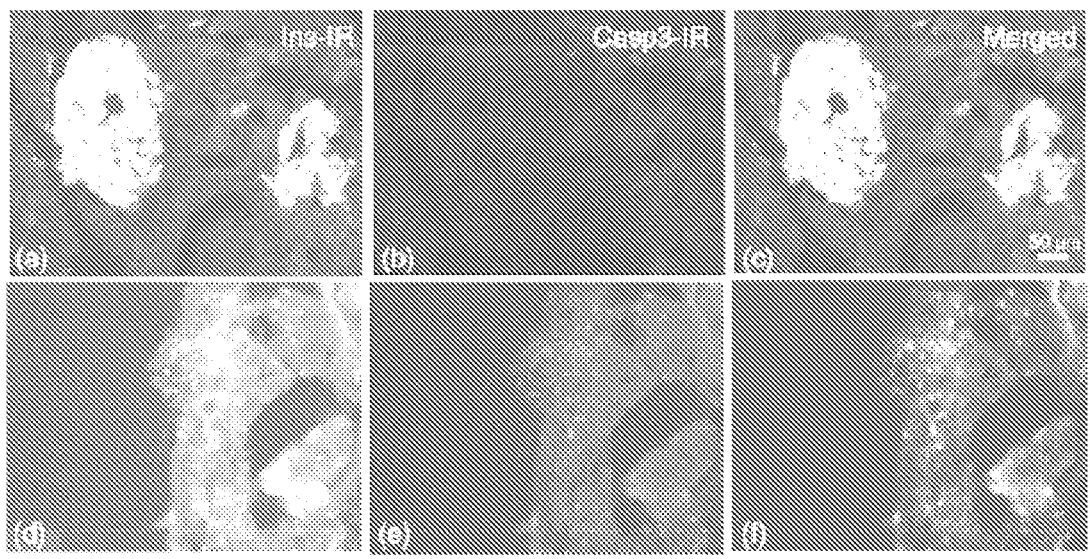
FIG. 6: Assessment of insulin production and apoptosis in pancreatic β-cells. Insulin immunoreactivity in Langerhans islets of a mouse gavaged with CTB-Pins (A). Caspase-3 immunostaining in the same section is shown in the red channel (B). Merged picture of A and B is shown in C. A view of the pancreas which shows the remnant of a large Langerhans islet of the mouse gavaged with untransformed plant leaf material (D). Caspase-3 immunoreactivity in the same section taken in red channel (E). Merged picture of D and E (F).

Preservation of the Insulin Producing β-Cells Following Oral Delivery of CTB-Pins It was desired to determine if the remaining β-cells represented in the pancreata of the different treatment groups were apoptotic. Because cellular infiltration can lead to apoptosis, this could be used as a hallmark to study type 1 diabetes (Riedl and Shi, 2004). It was found that the β-cells from NOD mice administered CTB-Pins rarely expressed caspase-3, suggesting that apoptosis was prevented in these cells. In the other experimental groups, even the very few remaining insulin-producing P-cells expressed activated caspase-3, suggesting that they were undergoing apoptosis (FIG. 6).

Induction of Th2 Response and Production of Immunosuppressive Cytokines

Figure 7A:
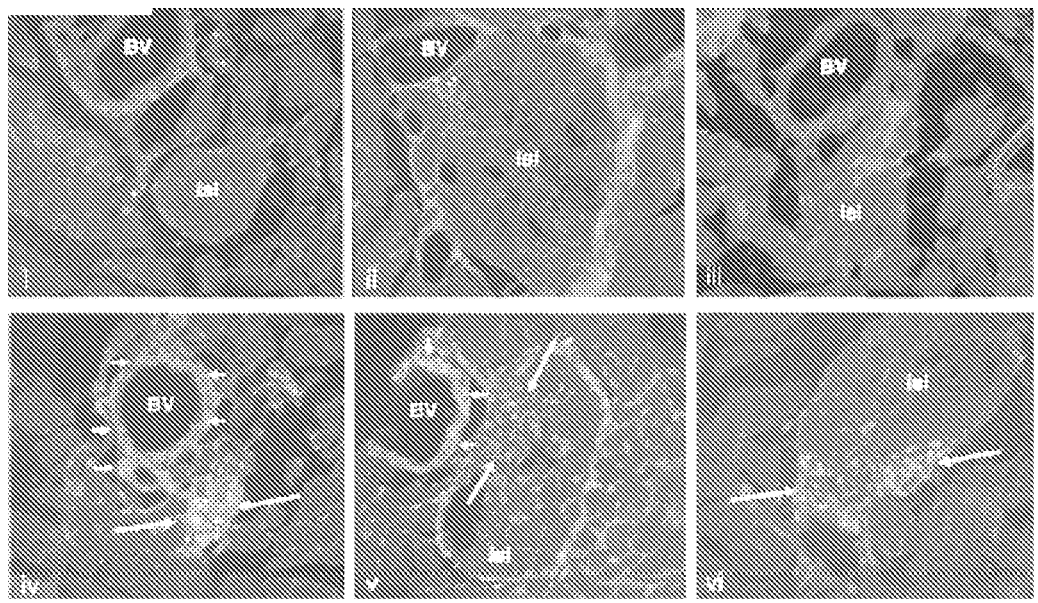
FIG. 7: Immunostaining for cytokine production. A) IL10 immunoreactivity in the pancreas of three mice administered untransformed plant leaf material (a), (b), and (c). Blood vessels (BV) and the langerhans islets (isl) are indicated. Photos (d), (e) and (f) show the islets of mice gavaged with CTB-Proinsulin. Small arrows indicate perivascular infiltration of IL10 expressing lymphocytes. Large arrows indicate IL10 positive lymphocytes inside or around the islets. B) IL4 immunoreactivity in the pancreas of mice gavaged with IFN-GFP, CTB-GFP or CTB-Pins plant leaf material. Small arrows indicate position of the islets.
Figure 7B:
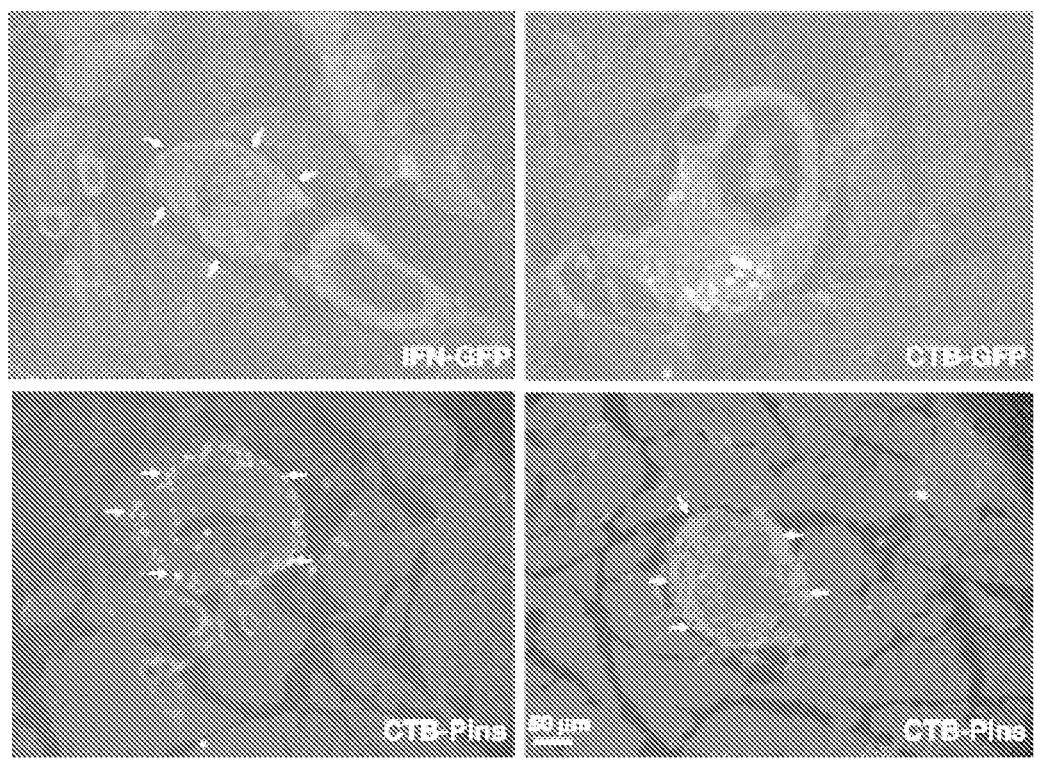

Oral administration of CTB-Pins to the NOD mice led to an increased recruitment of immunosuppressive cytokine-producing cells (lymphocytes) to the pancreas. A large number of IL10- or IL4-producing cells are seen proximal to the pancreatic islets, which are recruited through the circulation This process is supported by significant perivascular migration of IL4- and IL10-expressing cells seen in the pancreas of CTB-Pins treated NOD mice (FIGS. 7A&B).

Serum and Intestinal Immunoglobulin Levels Following Oral Delivery of CTB-Pins

Figure 8A:
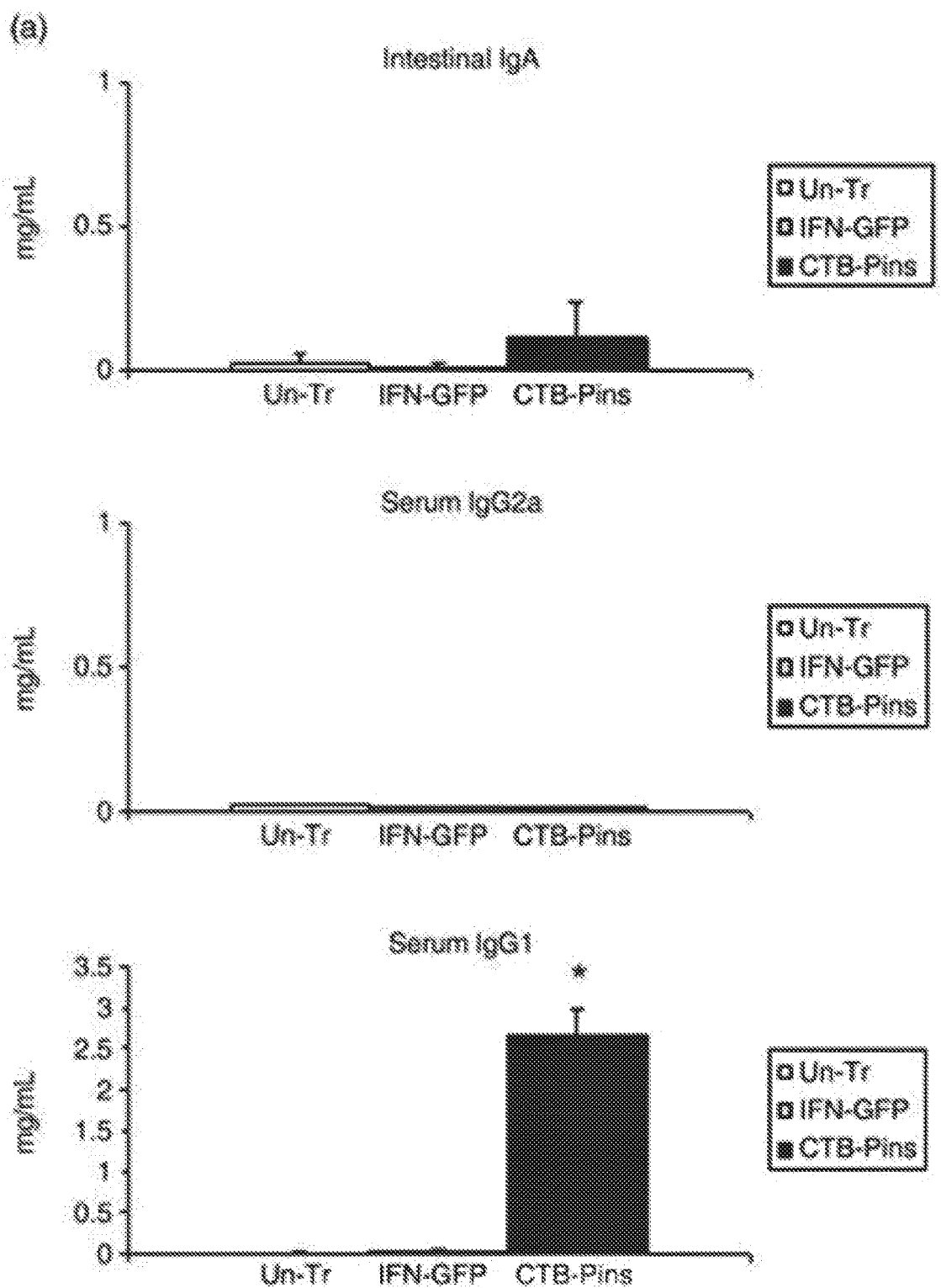
FIG. 8: Determination of immunoglobulin and glucose levels. A) Serum levels of IgA, IgG2a and IgG1 in NOD mice gavaged with CTB-Pins expressing plant leaf material as compared to the control groups gavaged with untransformed plant or IFN-GFP expressing leaf material. B) Blood and urine glucose levels in various groups of NOD mice after oral administration of CTB-Pins (6 weeks post treatment). n: Un-Tr=1, IFN-GFP=1, CTB-GFP=2, CTB-Pins=2. Using student T test, P value is less than 0.05; bars=standard deviation. 'n' designates the number of animals in each treatment group.

Serum and intestinal mucosal immunoglobulin (Ig) levels were determined by ELISA using CTB as the capture antigen. Serum levels of IgG1 increased in NOD mice treated with CTB-Pins expressing plant leaf material as compared to the control groups. There were low serum IgG2a and mucosal IgA levels against CTB observed among NOD mice treated with untransformed plant leaf material or plants expressing IFN-GFP or CTB-Pins (FIG. 8A).

Blood and Urine Glucose Levels of NOD Mice Treated with CTB-Human Proinsulin

Figure 8B:
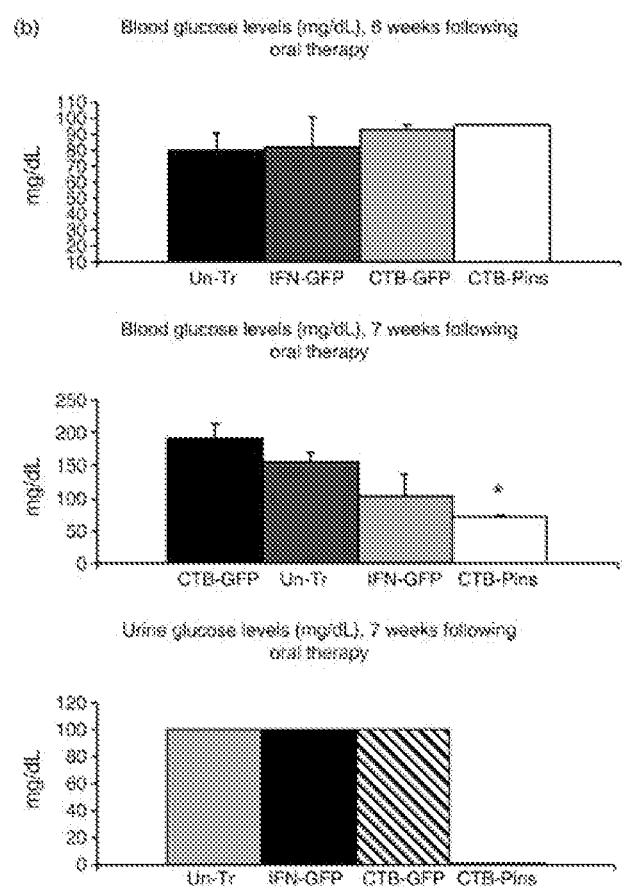

Blood and urine glucose levels of the treated NOD mice were measured twice, at weeks 6 and 7 of the treatment (11 and 12 week old mice). The blood glucose values of all groups in this study at both time points tested were below 200 mg/dl, and therefore not considered diabetic. This was not unforeseen, as NOD mice typically do not develop high blood glucose until 12-15 weeks age (Arakawa et al., 1998). Although, at week 11, the CTB-Pins treated group had a blood glucose level as high as the other control plant treated animals, interestingly, at week 12, the blood glucose level of the mice were rising, the CTB-Pins treated animals had a significantly lower blood glucose values than the control groups. Urine glucose values were also lower in the CTB-Pins treated group (FIG. 8B).

Discussion

Oral tolerance induced by the feeding of autoantigens has been applied successfully as a therapeutic tool in experimental models of autoimmune diseases (Strobel and Mowat, 1998). The basic mechanism of oral tolerance in humans has yet to be elucidated, and oral antigen administration regimens have resulted in limited success when applied to patients (Chaillous et al., 2000, Garside et al., 1999; Pozzilli et al., 2000). A possible explanation for the limited success could be due to the fact that the doses of the orally administered antigens to humans was low compared to those that were delivered to mice, considering the surface area of the intestinal absorptive epithelium (Pozzilli and Cavallo, 2000). In this case, CTB may serve as the necessary co-factor required to overcome the inefficient presentation of insulin to the mucosal T-cells, resulting from the limited transport of native insulin across the epithelial layer. In order for oral tolerance to become a realistic therapy for human autoimmune diseases, adjuvants that possess the ability to enhance the tolerogenic potential of orally delivered antigens need to be identified. The coupling of autoantigens—in this case, proinsulin—to the non-toxic Cholera toxin B subunit (CTB) dramatically increases their tolerogenic potential (Arakawa et al., 1998; Bergerot et al 1997; Sun et al, 1994). This effect is mediated by the ability of CTB to act as a transmucosal carrier, although CTB may have a direct affect on the immune system (Burkart et al, 1999; Li and Fox 1999). The current primary limitation in advancing this concept in clinical trials is the low levels of expression in transgenic plants (Bergerot et al., 1997). This limitation can be overcome by the hyper-expression of CTB-proinsulin fusion protein in transgenic chloroplasts.

Previous studies expressing CTB-proinsulin fusion protein in plants have been performed in potato (Arakawa et al, 1998). The expression level in nuclear transgenic potato tubers was 0.1% of tsp. The low expression level required feeding NOD mice with large amounts of fresh potatoes. In a previous work (PCT/US2006/021024), it was shown that CTB-proinsulin fusion protein accumulated in transplastomic tobacco up to ~16% of tsp, 160-fold greater than that achieved in nuclear transgenic potatoes. As such, the NOD mice were gavaged with 8 mg of the CTB-Pins tobacco leaf tissue (containing ~14 μg of the fusion protein) per week, which is a 375-fold reduction in the amount of plant tissue administered compared to the 3 g per week used previously (Arakawa et al., 1998). Using these small concentrated doses reduces the possibility of potential confounding effects of leaf tissue and eliminates the need to process or purify large quantities of plant material. Hyper-expression of CTB-Proinsulin in plant plastids should make this fusion protein abundantly available for animal studies or human clinical trials.

Furthermore, it has now been discovered by the inventor that CTB-Pins expression can occur in lettuce plastids. Accumulation was observed in transplastomic lettuce at an average value determined for lettuce (~1.8% tsp), which represents a level of protein sufficient to proceed with animal or preclinical studies. For example, in this study, approximately 14 μg CTB-Pins was delivered to NOD mice; a comparable dose could be derived from 100 mg of fresh lettuce leaf, a feasible quantity for weekly oral delivery. The difference observed between tobacco and lettuce may in part be attributed to the 5' regulatory elements used in the studies. Tobacco expression of CTB-Pins is driven by the endogenous psbA 5' UTR whereas lettuce expression is regulated by the inclusion of the translational control region of bacteriophage T7 gene 10. Previous studies involving the inventor have demonstrated that the level of foreign protein accumulation is less when these translation elements are used to drive expression of the same gene, with psbA 5' UTR being the more efficient (Dhingra et al., 2004). In addition, intrinsic variation in the nature of the leaves from tobacco and lettuce may influence the accumulation of foreign protein expressed in chloroplasts. In alternative embodiments, transformation constructs for lettuce for CTB-Pins expression employ lettuce endogenous translation elements such as psbA 5' UTR for further increasing the level of expression.

Oral administration of self antigens such as insulin leads to their uptake by the gut associated lymphoid tissue (GALT), including the intestinal mucosal M cells, which pass the antigen to underlying antigen presenting cells (Limaye et al., 2006). This leads to the activation of T-cells and induction of a Th2 cell response, which is characterized by the up-regulation of immunosuppressive cytokines (such as IL10 and IL4) and serum antibodies (such as IgG1 but not IgG2a, Faria and Weiner, 2005; Salmond et al., 2002). No significant increase in mucosal IgA was seen in the present study in CTB-Pins treated mice versus the control groups. CTB-Pins gavaged animals showed very high levels of IgG1 but not IgG2a whereas all control groups showed no variation (FIG. 8A). The serum IgG1 values of the CTB-Pins treated animals confirm activated the Th2 response, supported by the histological with less lymphocytic infiltration and upregulation of immunosuppressive cytokine levels in tissues of the CTB-Pins treated mice, supported by a trend in the blood and urine glucose levels which were higher in control groups than those of the CTB-Pins treated group. The presence of CTB in the intestine ensures an effective receptor-mediated oral delivery of intact plant-derived fusion protein across the intestinal mucosa via binding of CTB to the $GM_1$ ganglioside receptor and uptake by intestinal M cells and enterocytes.

Taken together, the data presented here suggest that the suppression of the insulitis was mediated by regulatory Th-2-cells. Since T-cell regulation is a major player in mucosal immunity, oral administration of an autoantigen can be used to treat autoimmune diseases in animal models by generating active T-cell suppression. Several autoimmune diseases and their antigens are known: multiple sclerosis (MBP and PLP), arthritis (type II collagen), uveitis (S-antigen and IRBP), myasthenia gravis (AChR) and thyroiditis (thyroglobin) (Hafler and Weiner, 1997). In the United States, there are 5.5 million people suffering from psoriasis, 3 million from Graves' disease, 2.5 million from rheumatoid arthritis, 2-5 million from vitiligo, 3.5 million from thyroiditis, 1-4 million from Sjogren's syndrome, 0.5 million from Crohn's disease and multiple sclerosis, 370,000 from type 1 diabetes, etc. Based on the teachings herein, compositions of chloroplast derived therapeutic antigens to such autoimmune diseases is possible.

5-week old mice were used in this study to demonstrate the alleviation of symptomatic pancreatic insulitis and preservation of insulin-producing β-cells in mice, a condition that mimics human type 1 diabetes. Based on the success of the concept in older mice (Harrison et al., 1996), this strategy is likely to work not only prior to the onset of diabetes, but also at later stages of this autoimmune disease and this will be explored in future experiments. One previous human clinical study on the oral delivery of insulin was unsuccessful (Skyler et al., 2005) because insulin was not protected from digestive enzymes and acid hydrolysis. Insulin was protected by bioencapsulation within plant cells. Based on the results obtained in this study, human clinical trials are initiated.

Experimental Procedures

Vector Construction

The human proinsulin gene was synthesized according to Prodromou and Pearl (1992). The PCR product was then cloned into the PCR 2.1 vector and the sequence verified. The psbA promoter and 5' untranslated region (UTR) was amplified from the tobacco chloroplast genome, followed by sub-cloning, and sequence verification. The promoter-5'UTR fragment was then spliced together with the cholera toxin B-subunit (CTB) and human proinsulin by overlap extension (Horton et al., 1989). The construct containing the 5'UTR-CTB, and a GPGP (gly-pro-gly-pro) hinge region introduced by mutagenesis to allow for the proper folding of each protein by reducing steric hindrance, followed by human proinsulin; was designated as 5CP. Following SalI/NotI digestion the fusion gene was ligated into the pLD-ctv chloroplast transformation vector (Daniell et al., 1998, 2004b)

The pUC-based *Lactuca sativa* long flanking plasmid (pLS-LF, FIG. 1A) was constructed to integrate foreign genes into the intergenic spacer region (ISR) between tRNA-Ile and tRNA-Ala genes of the plastid genome inverted repeat region. Oligionucleotide primers were derived from regions of known conservation in the *N. tabacum* plastome and carried end modifications for restriction enzyme sites for use in vector assembly. The full length genes for plastid tRNA-Ile (pos. 101 979-102 998) and tRNA-Ala (pos. 103 063-103 949) were amplified and ligated into the pUC19 backbone. A unique PvuII recognition site (pos. 103 002) between the two sequences facilitates insertion transformation cassettes. Long flanking sequences encoding the 3' end of the 16S (100 876-101 979; 810 bp) and the 5' end of the 23S (104 102-105 075; 974 bp) ribosomal RNA subunits included were amplified and cloned in kind. Numeric values correspond to positions in the *L. sativa* plastome (NC_007578). The transformation cassette (FIG. 1A) was assembled in pZERO (Invitrogen) and included the following published tobacco plastid regulatory sequence elements: ribosomal operon promoter (Prrn), rps16 and psbA 3' UTRs. The 5' translation control region of bacteriophage T7 gene 10 was used to drive CTB-Pins expression and the aadA gene was included with a GGAGG ribosome binding site. The expression cassette was flanked with SnaB1 recognition sites. The PvuII digested pLS-LF was treated with alkaline phosphatase prior to ligation with the SnaB1 digested cassette. Recovered plasmids were digested with SacI to determine correct orientation of the inserted cassette in pLS-LF. All cloning steps were carried out in *E. coli* according to the methods of Sambrook and Russel (2001).

Bombardment and Selection of Transgenic Plants

Bombardment and regeneration of *Nicotiana tabacum* cv Petite Havana transformants were carried out as previously described (Kumar and Daniell, 2004).

Seeds of *Lactuca sativa* v. Simpson elite (New England Seed Co.) were surface sterilized in a 3% hypochlorite solution, rinsed 3× in water and plated on Murashige and Skoog (MS) media solidified with 5.8 g $L^{-1}$ Phytablend® (Caisson). Young, fully expanded leaves ~4 $cm^2$ were placed adaxial side up on antibiotic free lettuce regeneration (LR) media (Kanamoto et al., 2006). Leaves were bombarded with 0.6 μm gold particles (BioRad) coated with pLS-LF-CTB-Pins (FIG. 1A) as described by Kumar and Daniell (2004) employing 900 psi rupture disks and a target distance of 6 cm. Samples were held in dark at 25° C. for two days prior to explant of $0.5^2$ cm pieces, adaxial side down onto LR media with 50 mg $L^{-1}$ spectinomycin dihydrochloride. Primary regenerants were screened by PCR for the transplastomic event and positive shoots were subjected to an additional regeneration cycle on spectinomycin LR media. Following the second regeneration shoots were rooted in half strength MS media with 0.1 mg $L^{-1}$ NAA and 50 mg $L^{-1}$ spectinomycin. Plants were propagated by rooting of nodal sections in half strength, hormone free MS with spectinomycin. Rooted cuttings were hardened in Jiffy® peat pots before transfer to the greenhouse for seed production. T1 seeds (achene) were harvested when pappus were present, allowed to dry at 24° C. Sterile seeds (100) were plated on MS media with 50 mg L$^{-1}$ spectinomycin Southern Blot Analysis Southern analysis was carried out essentially according to Kumar and Daniell (2004). Total tobacco DNA was digested with AflIII, separated on a 0.7% agarose gel at 45V for 4 hours, and then transferred to a nylon membrane. The pUC-CT vector DNA was digested with BamHI and BglII to generate a 0.8 kb probe which was used as a flanking probe and pLD-CTB-Pins was digested with MfeI and NotI to generate a 0.36 kb gene specific probe. After labeling the probe with $^{32}$P, hybridization of the membranes was done using QUICK-HYB hybridization solution and protocol (Stratagene, La Jolla, Calif.).

For lettuce transformants genomic DNA was digested to completion with BglII, separated on 0.7% TAE-agarose and transferred to nylon membranes. Plastid flanking sequence probe (1.3 kb) was amplified by PCR from lettuce genomic DNA. PCR product was purified and labeled probe was generated by incubation with $^{32}$P and Ready-To-Go™ DNA Labeling Beads (-dCTP) (GE Healthcare). Hybridization was carried out at 68° C. with washing at 37° C. and 60° C. Radiolabeled blots were exposed to film at −80° C. for 16 hr.

Western Blot and Densitometric Analysis

Total soluble protein (tsp) was isolated from rooted second regenerants of tobacco and lettuce. Approximately 100 mg of leaf tissue, separated by SDS-PAGE and transferred to nitrocellulose membranes for immunoblotting according to Kumar and Daniell (2004). Anti-proinsulin monoclonal antibody (American Qualex, 1:20 000) and goat anti-mouse IgG conjugated to horse radish peroxidase (American Qualex, 1:15 000) were use for detection of the CTB-Pins protein. Immunoblotting with anti-CTB primary (1:4000, Sigma) and donkey anti-rabbit HRP conjugate secondary antibody (1:12 500, Biomeda) was employed for spot densitometric analysis. For transplastomic lettuce samples 36 µg of tsp was added to each well and for transplastomic tobacco samples 6 µg of tsp was added to each well. The standards (CTB; Sigma) contained 25 ng, 50 ng, and 100 ng of purified bacterial CTB. SuperSignal® West Pico HRP substrate kit (Pierce) was used for autoradiographic detection. Following exposure to film the blots were analyzed for presence of CTB-Pins using the AlphaImager® and AlphaEase® FC software (Alpha Innotech) by comparison to known quantities of standard.

GM$_1$ Binding Assay

In order to test the ability of chloroplast derived CTB-Pins to bind to GM$_1$ receptor a CTB-GM$_1$ binding assay was performed. Tobacco extracts were prepared in ELISA buffer and lettuce extracts were prepared in western extraction buffer. Ninety-six well plates were incubated with monosialoganglioside-GM$_1$ (Sigma) (3.0 µg/ml in bicarbonate buffer) and BSA as a control and incubated overnight at 4° C. Following washing 3× each with PBST and sterile water, the plate was blocked with PTM (tobacco) or 0.25% BSA in PBS (lettuce) for 1 hr at 37° C. CTB standards (Sigma) and soluble protein extracts were diluted in ELISA plant extraction buffer (without Tween 20 and PMSF). The standards and samples were then added in duplicate and incubated at 4° C. overnight. Rabbit anti-CTB primary antibody (1:8000 tobacco, 1:3000 lettuce; Sigma) and horseradish peroxidase conjugated donkey anti-rabbit secondary antibody (1:25 000 tobacco and 1: 12 500 lettuce; Biomeda) was used to detect the binding of CTB-Pins to GM$_1$ receptor. The plate was washed thrice with both PBST and sterile water, and 100 µl of TMB soluble solution substrate (American Qualex) was added to the wells and incubated in the dark for 30 min. The reaction was stopped with 50 µl 2M H$_2$SO$_4$, and then read on a plate reader (Dynex Technologies) at 450 nm.

Animal Studies

Four week old female non-obese diabetic (NOD) mice were purchased from The Jackson Laboratory (Bar Harbor, Me.). Mice were kept in the UCF Wild Animal Facility under normal light/dark cycle conditions and had access to food and water ad lib. Treatment by means of oral administration of cholera toxin B subunit-Proinsulin (CTB-Pins) expressing transgenic tobacco or control plant leaf material began when animals were 5 weeks old, to allow the mice one week to acclimate to the facility. Mice were divided into the following groups: group 1 received untransformed plant leaf material (Un-Tr); group 2 received transgenic plant leaf expressing Cholera toxin B subunit conjugated to GFP (CTB-GFP); group 3 received transgenic plant leaf expressing interferon conjugated to GFP (IFN-GFP); and group 4 received CTB-Pins expressing transgenic plant leaf. Each group contained five animals, except the CTB-Pins group, which contained seven. Mice were administered 14 µg of the specified ground tobacco leaf material diluted in 200 µl of PBS (0.1M) by careful gavage into the hypopharynx once a week for 7 weeks. For preparation of the gavage material, leaves were frozen and ground in liquid nitrogen. For oral delivery, 8 mg of the CTB-Pins expressing plant leaf material contained 14 µg of the CTB-Pins protein. For the untransformed leaf material, 8 mg of the ground plant material was given to mimic a similar oral dose as the CTB-Pins group. The CTB-GFP and IFN-GFP levels were similar to CTB-Pins. The animals were sacrificed at 12 weeks of age, the pancreas and other tissues were collected, and both blood and urine glucose levels were measured.

Histochemistry for Lymphocytic Infiltration and Insulitis

Following the 7 week treatment, mice were sacrificed and perfused transcardially with 10 ml of PBS followed by 50 ml of 4% paraformaldehyde (PFA) in 0.1M PBS. Part of the pancreas was removed before the fixation and freshly frozen in tissue Tec freezing medium (Vector labs). The pancreas was removed, post-fixed overnight in 4% PFA, and then cryo-protected by serially passing through 10%, 20% and 30% sucrose solutions in PBS. The pancreatic tissue was then immersed in Tissue Tec freezing medium and frozen (Samsam et al., 2003) in liquid nitrogen-cooled isomethylbuthane (isopathane, Sigma). Ten micrometer (µm) thick frozen sections of the pancreas were then prepared using a cryostat. Pancreas cryosections were stained with Hematoxillin and Eosin, dehydrated in serial graded alcohol solutions, and the slides were covered.

Insulitis levels were measured based on the extent of the lymphocyte infiltration of the islets of Langerhans. At least 50 sections per animal were scored, the degree of insulitis was scored based on a 5 level scale ranging from 1-5, where score 1 is a normal islet with no sign of T-cell infiltration, and score 5 indicates maximal infiltration and development of insulitis.

Immunohistochemistry for Insulin, Caspase-3, IL4 and IL10

Immunohistochemistry for the localization of insulin, caspase-3 (a final molecule of apoptosis), and the immunosuppressive cytokines IL4 and IL10 were performed on the pancreas cryosections. Sections were blocked with 10% BSA (bovine serum albumin) containing 0.3% Triton-X 100.

Polyclonal guinea pig anti-insulin, polyclonal rabbit anti-caspase-3, rat monoclonal anti-IL4 and anti-IL10 primary antibodies (Invitrogen) were diluted at a concentration of 1:300 in 1% BSA in PBS containing 0.3% Triton-X. Fluorescent conjugated secondary antibodies were goat anti-guinea pig-Alexa Fluor 488 (green), goat anti-rabbit-Alexa Fluor 555 (red), and goat anti-rat Alexa Fluor 555 (red, Invitrogen).

Antibody Titer

Serum and intestinal antibodies were assayed for the presence of anti-CTB antibodies using calorimetric ELISA methods. Following sacrifice and prior to transcardial perfusion, 200-300 µl of blood was collected from retro-bulbar vein. Serum was extracted after 15 min centrifuge at 5K rpm at 4° C. for antibody titer. Ninety-six well plates were coated with CTB (Sigma). Serial dilutions of serum or supernatants of fecal pellets (5 pellets per sample were weighed and diluted in 0.1M PBS) collected from the different animal groups were added to the coated plate wells. For standard values (isotype control) and determination of antibody level, the standard columns of the plate were coated with serial dilutions of purified mouse IgG1 or IgG2a, or IgA protein (Pharmingen) and ELISA was performed. Secondary antibodies were horseradish peroxidase (HRP)-conjugated anti-mouse IgG2a, IgG1, or IgA antibodies (BD Pharmingen, USA) at a concentration of 1:3000 in PBS containing 0.1% Tween-20 and 3% milk powder. The plates were washed with 200 µl of PBS, and the substrate tetra-methyl benzidine (TMB) was added to the wells and incubated in the dark at 37° C. for 20 minutes. The reaction was stopped by adding 50 µl of $H_2SO_4$ and the plates were read on a plate reader (Dynex Technologies) at 450 nm.

Blood and Urine Glucose Levels

Blood and urine glucose levels were measured for two consequent weeks (11 and 12 weeks old, or 6 and 7 weeks following oral delivery of various plant leaf material) with urinary glucose test strips (Clinistix and Diastix, Bayer), and blood glucose was measured by bleeding from either the tail vein or the retro-bulbar vein (at week 12, before sacrificing) by means of a blood glucose analyzer (Boehringer Mannheim). Blood glucose levels over 250 mg/dl were considered diabetic (Arakawa et al, 1998). The first blood sample was taken by a small cut on the tail and extraction of one drop of blood onto the specific strips provided by the manufacturer which were already fed onto the glucose analyzer. The second blood sample was taken from the retro-bulbar vein after deep (lethal) inhalation anesthesia with isoflurane before transcardial perfusion of 4% paraformaldehyde Urine sample was collected by pressing on the supra-pubic area and squeezing 1-2 drops of urine out onto the urine strips provided by the manufacturer.

REFERENCES

Arakawa, T., Yu, J., Chong, D., Hough, J., Engen, P. and Langridge, W. (1998). A plant-bases cholera toxin B subunit-insulin fusion protein protects against the development of autoimmune diabetes. Nature, 16, 934-938.

Arlen, P. A., Falconer, R., Cherukumilli, S., Cole, A., Cole, A. M., Oishi, K. and Daniell, H. (2007) Field production and functional evaluation of chloroplast-derived interferon alpha 2b. Plant Biotecnol J, Accepted with minor revision.

Bergerot, I., Ploix, C., Petersen, J., Moulin. V., Rask, C. and Fabien, N. (1997) A cholera toxoid-insulin conjugate as an oral vaccine against spontaneous autoimmune diabetes. Proc Natl Acad Sci USA, 94, 4610-4614.

Birch-Machin, I., Newell, C. A., Hibberd, J. M. and Gray, J. C. (2004) Accumulation of rotavirus VP6 protein in chloroplasts of transplastomic tobacco is limited by protein stability. Plant Biotech J, 2, 261-270.

Burkart, V., Kim, Y., Kauer, M. and Kolb, H. (1999) Induction of tolerance in macrophages by cholera toxin B chain. Pathobiology, 67, 314-317.

Chaillous, L., Lefevre, H., Thivolet, C., Boitard, C., Lahlou, N., Atlan-Gepner, C., Bouhanick, B., Mogenet, A., Nicolino, M., Carel, J. C., Lecomte, P., Marechaud, R., Bougneres, P., Charbonnel, B. and Sai, P. (2000) Oral insulin administration and residual beta-cell function in recent onset type 1 Diabetes: a multicentre randomised controlled trial. Diabete Insuline Orale group. Lancet, 356, 545-549.

Chebolu, S. and Daniell, H. (2007) Stable expression of GAL/GALNAc lectin of Entamoeba histolytica in transgenic chloroplast and immunogenicity in mice towards vaccine development for amebiasis. Plant Biotech J, 2, 230-239.

Daniell, H. (2002) Molecular strategies for gene containment in transgenic crops. Nat Biotechnol, 20, 581-586.

Daniell, H., Carmona-Sanchez, O. and Burns, B. (2004a) Chloroplast derived antibodies, biopharmaceuticals and edible vaccines. In: Molecular Farming (Fischer, R. and Schillberg, S., eds), pp. 113-133, Weinheim: WILEY-VCH Verlag.

Daniell, H., Chebolu, S., Kumar, S., Singleton, M. and Falconer, R. (2005a) Chloroplast-derived vaccine antigens and other therapeutic proteins. Vaccine, 23, 1779-1783.

Daniell, H., Datta, R., Varma, S., Gray, S. and Lee, S. B. (1998) Containment of herbicide resistance through genetic engineering of the chloroplast genome. Nat Biotechnol, 16, 345-348.

Daniell, H., Kumar, S. and Dufourmantel, N. (2005b) Breakthrough in chloroplast genetic engineering of agronomically important crops. Trends Biotechnol, 23, 238-245.

Daniell, H., Lee, S. B., Panchal, T. and Wiebe, P. O. (2001) Expression of cholera toxin B subunit gene and assembly as functional oligomers in transgenic tobacco chloroplasts. J Mol Biol, 311, 1001-1009.

Daniell, H., Ruiz, O. N. and Dhingra, A. (2004b) Chloroplast genetic engineering to improve agronomic traits. Methods Mol Biol, 286, 111-137.

De Cosa, B., Moar, W., Lee, S. B., Miller, M. and Daniell, H. (2001) Overexpression of the Bt cry2Aa2 operon in chloroplasts leads to formation of insecticidal crystals. Nat Biotechnol, 19, 71-74.

DeGray, G., Rajasekaran, K., Smith, F., Sanford, J. and Daniell, H. (2001) Expression of an antimicrobial peptide via the chloroplast genome to control phytopathogenic bacteria and fungi. Plant Physiol, 127, 852-862.

De Haan, L., Verweij, W. R., Feil, I. K., Holtrop, M., Hol, W. G. J., Agsteribbe, E. and Wilschut, J. (1998) Role of GM1 binding in the mucosal immunogenicity and adjuvant activity of the Escherchia coli heat-labile enterotoxin and its B subunit. Immunology, 94, 424-430.

Dertzbaugh, M. T. and Cox, L. M. (1998) The affinity of cholera toxin for $Ni^{2+}$ ion. Protein Eng, 11, 577-581.

Dhingra, A., Portis Jr., A. R, Daniell, H. (2004) Enhanced translation of a chloroplast-expressed RbcS gene restores small subunit levels and photosynthesis in nuclear RbcS antisense plants. Proc Natl Acad Sci 101,6315-6320.

Faria, A. M. and Weiner, H. L. (2005) Oral tolerance. Immunol Rev, 206, 232-59.

Fernandez-San Millan, A., Mingeo-Castel, A. M., Miller, M. and Daniell, H. (2003) A chloroplast transgenic approach to hyper-express and purify Human Serum Albumin, a protein highly susceptible to proteolytic degradation. *Plant Biotech J,* 1, 71-79.

Garside, P., Mowat, A. M. and Khoruts, A. (1999) Oral tolerance in disease. *Gut,* 44, 137-142.

Grevich, J. J., and Daniell, H. (2005) Chloroplast genetic engineering: Recent advances and future perspectives. *Crit Rev in Plant Sci,* 24, 83-107.

Guda, C., Lee, S. B. and Daniell, H. (2000) Stable expression of biodegradable protein based polymer in tobacco chloroplasts. *Plant Cell Rep,* 19, 257-262.

Hafler, D. A. and Weiner, H. L. (1997) Oral tolerance for the treatment of autoimmune diseases. In: *Novel Therapeutic Agents for the Treatment of Autoimmune Diseases.* (Simon, L. S., Strand, V., Scott D. L., eds), pp. 201-220 New York: Marcel Dekker Inc.

Harrison, L. C., Dempsey-Collier, M., Kramer, D. R. and Takahashi, K. (1996) Insulin induces regulatory CD8 T Cells that prevent murine insulin-dependent diabetes. *J Exp Med,* 184, 2167-2174.

Holmgren, J., Adamsson, J., Anjuere, F., Clemens, J., Czerkinsky, C., Eriksson, K., Flach, C. F., George-Chandy, A., Harandi, A. M., Lebens, M., Lehner, T., Lindblad, M., Nygren, E., Raghavan, S., Sanchez, J., Stanford, M., Sun, J. B., Svennerholm, A. M. and Tengvall, S. (2005) Mucosal adjuvants and anti-infection and anti-immunopathology vaccines based on cholera toxin, cholera toxin B subunit and CpG DNA. *Immunol Lett,* 97,181-188.

Homann, D., Dyrberg, T., Petersen, J., Oldstone, M. B. and von Herrath, M. G. (1999) Insulin in oral immune (tolerance): a one-amino acid change in the B chain makes the difference. *J Immunol,* 163, 1833-1838.

Horton, R. M., Hunt, H. D., Ho, S. N., Pullen, J. K. and Pease, L. R. (1989) Engineering hybrid genes without the use of restriction enzymes: gene splicing by overlap extension. *Gene,* 77, 61-68.

Kamarajugadda, S. and Daniell, H. (2006) Choroplast derived anthrax and other vaccine antigens: their immunogenic and immunoprotective properties. *Expert Rev Vaccines,* 5, 839-849.

Kanamoto, H., Yamashita, A., Asao, H., Okumura, S., Takase, H., Hattori, M., Yokota, A. and Tomizawa, K. (2006) Efficient and stable transformation of *Lactuca sativa* L. cv. Cisco (lettuce) plastids. *Transgenic Res,* 15, 205-217.

Koya, V., Moayeri, M., Leppla, S. H. and Daniell, H. (2005) Plant-based vaccine: mice immunized with chloroplast-derived anthrax protective antigen survive anthrax lethal toxin challenge. *Infect Immun,* 73, 8266-8274.

Kumar, S. and Daniell, H. (2004) Engineering the chloroplast genome for hyperexpression of human therapeutic proteins and vaccine antigens. *Methods Mol Biol,* 267, 365-383.

Kumar, S., Dhingra, A. and Daniell, H. (2004a) Plastid-expressed betaine aldehyde dehydrogenase gene in carrot cultured cells, roots, and leaves confer enhanced salt tolerance. *Plant Physiol,* 136, 2843-2854

Kumar, S., Dhingra, A. and Daniell, H. (2004b) Stable transformation of the cotton plastid genome and maternal inheritance of transgenes. *Plant Mol Biol,* 56, 203-216.

Lee, S. B., Kwon, H. B., Kwon, S. J., Park, S. C., Jeong, M. J., Han, S. E., Byun, M. O. and Daniell, H. (2003) Accumulation of trehalose within transgenic chloroplasts confers drought tolerance. *Mol Breed,* 11, 1-13.

Leelavathi, S. and Reddy, V. S. (2003) Chloroplast expression of His-tagged GUS-fusions: a general strategy to overproduce and purify foreign proteins using transplastomic plants as bioreactors. *Mol Breed,* 11, 49-58.

Lelivelt, C. L., McCabe, M. S., Newell, C. A., Desnoo, C. B., van Dun, K. M., Birch-Machin, I., Gray, J. C., Mills, K. H. and Nugent, J. M. (2005) Stable plastid transformation in lettuce (*Lactuca sativa* L.). *Plant Mol Biol,* 58, 763-774.

Li, T. K. and Fox, B. S. (1999) Cholera toxin B subunit binding to an antigen-presenting cell directly co-stimulates cytokine production from a T cell clone. *Int Immunol,* 8, 1849-1856.

Limaye, A., Koya, V., Samsam, M. and Daniell, H. (2006) Receptor mediated oral delivery green fluorescent protein expressed in transgenic chloroplasts into the mouse circulatory system. *FASEB J.* 20, 959-961.

Ludwig, D. S., Holmes, R. K. and Schoolnik, G. K. (1985) Chemical and immunochemical studies on the receptor binding domain of cholera toxin B subunit. *J Biol Chem,* 260,12528-12534.

Ma, J. K. C., Drake, P. M. W. and Christou, P. (2003) The production of recombinant pharmaceutical proteins in plants. *Nat Rev Genet,* 4,794-805.

Merritt, E. A., Sarfaty, S., van den Akker, F., L'Hoir, C., Martial, J. A. and Hol, W. G. (1994) Crystal structure of cholera toxin B-pentamer bound to receptor GM1 pentasaccharide. *Prot Sci,* 3,166-175.

Molina, A., Herva-Stubbs, S., Daniell, H., Mingo-Castel, A. M. and Veramendi, J. (2004) High yield expression of a viral peptide animal vaccine in transgenic tobacco chloroplasts. *Plant Biotech J,* 2,141-153.

Nagata, M., Santamaria, P., Kawamura, T., Utsugi, T. and Yoon, J. W. (1994) Evidence for the role of CD8+ cytotoxic T cells in the destruction of pancreatic beta-cells in nonobese diabetic mice. *J Immunol,* 152, 2042-2050.

Ploix, C., Bergerot, I., Durand, A., Czerkinsky, C., Holmgren, J. and Thivolet, C. (1999) Oral administration of cholera toxin B-insulin conjugates protects NOD mice from autoimmune diabetes by inducing CD4+ regulatory T-cells. *Diabetes,* 48, 2150-2156.

Pozzilli, P. and Cavallo, G. M. (2000) Oral insulin and the induction of tolerance in man: reality or fantasy? *Diabetes Metab Rev,* 16, 306-307.

Pozzilli, P., Pitocco, D., Visalli, N., Cavallo, M. G., Buzzetti, R., Crino, A., Spera, S., Suraci, C., Multari, G., Cervoni, M., Manca Bitti, M. L., Matteoli, M. C., Marietti, G., Ferrazzoli, F., Cassone Faldetta, M. R., Giordano, C., Sbriglia, M., Sarugeri, E. and Ghirlanda, G. (2000) No effect of oral insulin on residual beta-cell function in recent-onset type I diabetes (the IMDIAB VII). IMDIAB Group. *Diabetologia,* 43, 1000-1004.

Prodromou, C. and Pearl, L. H. (1992) Recursive PCR: a novel technique for total gene synthesis. *Protein Eng,* 5, 827-829.

Quesada-Vargas, T., Ruiz, O. N. and Daniell H. (2005) Characterization of heterologous multigene operons in transgenic chloroplasts: transcription, processing, and translation. *Plant Physiol,* 138, 1746-1762.

Riedl, S. J. and Shi, Y. (2004) Molecular mechanisms of caspase regulation during apoptosis. *Nat Rev Mol Cell Biol,* 5, 897-907.

Rigano, M. M. and Walmsley, A. M. (2005) Expression systems and developments in plant-made vaccines. *Immunol Cell Biol,* 83, 271-277.

Ruf, S., Hermann, M., Berger, I. J., Carrer, H. and Bock, R. (2001) Stable genetic transformation of tomato plastids and expression of a foreign protein in fruit. *Nat Biotechnol,* 19, 870-875.

Salmond, R. J., Luross, J. A. and Williams, N. A. (2002) Immune modulation by the cholera-like enterotoxins. *Expert Rev Mol Med.* 4, 1-16.

Sambrook, J., Fritsch, E. F. and Maniatis, T. (2001) Molecular Cloning: A Laboratory Manual, 3rd edn. Cold Spring Harbor: Cold Spring Harbor Laboratory Press.

Samsam, M., Mi, W., Wessig, C., Zielasek, J., Toyka, K. V., Coleman, M. P. and Martini, R. (2003) The W1ds mutation delays robust loss of motor and sensory axons in a genetic model for myelin-related axonopathy. *J Neurosci,* 23, 2833-2839.

Skyler, J. S., Krishner, J. P., Wolfsdorf, J., Cowie, C., Plamer, J. P., Greenbaum, C., Cuthbertson, D., Rafkin-Mervis, L. E., Chase, H. P. and Leschek, E. (2005) Effects of oral insulin in relatives of patients with type 1 diabetes. *Diabetes Care.* 28, 1068-1076.

Staub, J. M., Garcia, B., Graves, J., Hajdukiewicz, P. T., Hunter, P., Nehra, N., Paradkar, V., Schlittler, M., Carroll, J. A., Spatola, L., Ward, D., Ye, G., and Russell, D. A. (2000) High-yield production of a human therapeutic protein in tobacco chloroplasts. *Nat Biotechnol,* 18, 333-338.

Stern, D. B. and Gruissem, W. (1987) Control of plastid gene expression: 3' inverted repeats act as mRNA processing and stabilizing elements, but do not terminate transcription. *Cell,* 51, 1145-1157.

Strobel, S. and Mowat, A. M. (1998) Immune responses to dietary antigens: oral tolerance. *Immunol Today,* 4, 173-181.

Sun, J-B., Holmgren, J. and Czerkinsky, C. (1994) Cholera toxin B subunit: an efficient transmucosal carrier-delivery system for induction of peripheral immunological tolerance. *Proc Natl Acad Sci USA,* 91, 10795-10799.

Tregoning, J. S., Nixon, P., Kuroda, H., Svab, Z., Clare, S., Bowe, F., Fairweather, N., Ytterberg, J., van Wijk, K. J., Dougan, G. and Maliga, P. (2003) Expression of tetanus toxin fragment C in tobacco chloroplasts. *Nucleic Acids Res,* 31, 1174-1179.

Walmsley, A. M., Alvarez, M. L., Jin, Y., Kirk, D. D., Lee, S. M., Pinkhasov, J., Rigano, M. M., Arntzen, C. J. and Mason, H. S. (2003) Expression of the B subunit of *Escherichia coli* heat-labile enterotoxin as a fusion protein in transgenic tomato *Plant Cell Rep,* 21, 1020-1026.

Watson, J., Koya, V., Leppla, S. H. and Daniell, H (2004) Expression of *Bacillus anthracis* protective antigen in transgenic chloroplasts of tobacco, a non food/feed crop. *Vaccine,* 22, 4372-4384.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989); Methods in Plant Molecular Biology, Maliga et al, Eds., Cold Spring Harbor Laboratory Press, New York (1995); Arabidopsis, Meyerowitz et al, Eds., Cold Spring Harbor Laboratory Press, New York (1994) and the various references cited therein. U.S. Patent Publication 20030009783 and 20060031964 are also cited for plant transformation techniques.

Finally, while various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims. The teachings of all patents and other references cited herein are incorporated herein by reference in their entirety to the extent they are not inconsistent with the teachings herein.

What is claimed is:

1. A *Lactuca sativa* homoplasmic plant cell for producing cholera toxin B subunit-proinsulin (CTB-Pins) comprising plastids transformed to express CTB-Pins, said plastids comprising an expression cassette of the following operably linked components, a promoter operative in said plastid, a selectable marker sequence, a psbA 5' UTR translation element endogenous to *Lactuca sativa*, a heterologous polynucleotide sequence encoding said proinsulin expressed as a fusion protein conjugated to cholera toxin B subunit (CTB), and a transcription terminator functional in said plastid, said expression cassette being flanked by sequences which are homologous to DNA sequences of the *Lactuca sativa* plastid and facilitate homologous recombination of said expression cassette into said *Lactuca sativa* plastid genome in the intergenic region between trnI and trnA genes, said selectable marker sequence encoding an antibiotic-free selectable marker, wherein said plant cell produces a lettuce plant producing cholera toxin B subunit-proinsulin upon propagation.

2. An orally-administrable composition comprising a pharmaceutical protein of interest bioencapsulated in a *Lactuca sativa* plastid from a homoplasmic lettuce plant cell; said plastid comprising a plastid genome stably transformed with an expression cassette comprising, as operably linked components, a promoter operative in said plastid, a selectable marker sequence, a psbA 5' UTR translation element endogenous to *Lactuca sativa*, a heterologous polynucleotide sequence encoding said pharmaceutical protein of interest conjugated to nucleic acid encoding a cholera toxin B subunit, and a transcription terminator functional in said plastid, said expression cassette being flanked by sequences which are homologous to DNA sequences of the *Lactuca sativa* plastid and facilitate homologous recombination of said expression vector into said *Lactuca sativa* plastid genome in the intergenic region between trnI and trnA genes, wherein said pharmaceutical protein is proinsulin-CTB which reduces apoptosis in beta cells of the pancreas and increases recruitment of immunosuppressive cytokine producing cells to the pancreas upon oral administration to a subject.

3. A method of retarding the development of or treating diabetes in a subject in need thereof, said method comprising administering to said subject the composition as claimed in claim 2, said composition further comprising a plant remnant.

4. A stably transformed *Lactuca sativa* plant which comprises the plant cell of claim 1 or the recombinant progeny of said plant.

5. A method of producing a cholera toxin B subunit-proinsulin containing composition, said method comprising:

obtaining the stably transformed *Lactuca sativa* plant of claim 4 and homogenizing material of said stably transformed *Lactuca sativa* plant to produce homogenized material.

6. The method of claim 5, further comprising purifying cholera toxin B subunit-proinsulin from said homogenized material.

7. The method of claim 5, further comprising encapsulating said homogenized material.

8. The method of claim 7, wherein said homogenized material is not cooked prior to encapsulation.

9. The method of claim 5, wherein said homogenized material is dried to produce a powder.

10. The method of claim 9, further comprising encapsulating said powder.

* * * * *